United States Patent
Cooke et al.

(10) Patent No.: US 8,960,194 B2
(45) Date of Patent: Feb. 24, 2015

(54) VENTILATOR FOR RAPID RESPONSE TO RESPIRATORY DISEASE CONDITIONS

(75) Inventors: Richard Henry Cooke, Essex (GB); Nicholas Ong, Bellevue, WA (US); Roy Hays, Seattle, WA (US); David Kevin Hinton, Renton, WA (US); Theodore Scott Hergert, Redmond, WA (US); Jeffrey Jay Gilham, Sammamish, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 612 days.

(21) Appl. No.: 12/703,140

(22) Filed: Feb. 9, 2010

(65) Prior Publication Data

US 2010/0306992 A1 Dec. 9, 2010

Related U.S. Application Data

(63) Continuation-in-part of application No. 11/678,201, filed on Feb. 23, 2007, now abandoned, and a continuation-in-part of application No. 11/871,341, filed on Oct. 12, 2007, now Pat. No. 8,714,156.

(Continued)

(51) Int. Cl.
*A62B 9/02* (2006.01)
*A62B 9/00* (2006.01)
(Continued)

(52) U.S. Cl.
CPC ........... *A61M 16/20* (2013.01); *A61M 16/0409* (2014.02); *A61M 16/127* (2014.02); *A61M 16/204* (2014.02); *A61M 16/205* (2014.02); *A61M 16/207* (2014.02); *A61M 16/0434* (2013.01); *A61M 2016/0015* (2013.01);
(Continued)

(58) Field of Classification Search
USPC .............. 128/204.18, 204.21, 205.23, 205.24
See application file for complete search history.

(56) References Cited

U.S. PATENT DOCUMENTS 3,682,166 A   8/1972   Jacobs
3,961,624 A *   6/1976   Weigl ....................... 128/205.23
(Continued)

FOREIGN PATENT DOCUMENTS

GB   1491745 A   11/1977
GB   1582899 A   1/1981
GB   2101896 A   1/1983

OTHER PUBLICATIONS

L.S.S. Wong and N.M. McGuire, Laboratory assessment of the Bird T-Bird VA ventilator performance using a model lung, Feb. 2, 2000, British Journal of Anesthesia 84 (6):811-7.*
International Search Report for PCT/US07/62747, Mar. 3, 2008, International Search Authority.

(Continued)

*Primary Examiner* — Rachel Young
(74) *Attorney, Agent, or Firm* — Novel IP

(57) ABSTRACT

The present specification discloses a ventilator system that can be manufactured quickly with minimal skill requirements and rapidly deployed in response to epidemic respiratory disease conditions. In one embodiment, the ventilator, having a minimal number of controls, is used to give ventilation or mechanical breathing to a patient suffering ARDS. The mechanical ventilation is based on pressure control and has variable pressure, breathing rate, and oxygenation. Preferably, the ventilator is rapidly deployable, easy and intuitive to operate, and capable of sustaining at least 75% of epidemic respiratory distress victims who require assisted ventilation until resuming normal breathing.

17 Claims, 22 Drawing Sheets

Related U.S. Application Data

(60) Provisional application No. 61/151,443, filed on Feb. 10, 2009, provisional application No. 60/776,493, filed on Feb. 23, 2006, provisional application No. 60/829,502, filed on Oct. 13, 2006.

(51) Int. Cl.
| | | |
|---|---|---|
| *A61M 16/00* | (2006.01) | |
| *A61M 16/20* | (2006.01) | |
| *A61M 16/04* | (2006.01) | |
| *A61M 16/12* | (2006.01) | |

(52) U.S. Cl.
CPC ............... *A61M2016/0021* (2013.01); *A61M 2016/0027* (2013.01); *A61M 2202/0208* (2013.01); *A61M 2205/18* (2013.01); *A61M 2205/581* (2013.01); *A61M 2205/587* (2013.01); *A61M 2205/8206* (2013.01); *A61M 2209/06* (2013.01)
USPC ............ 128/205.24; 128/205.23; 128/204.18

(56) References Cited

U.S. PATENT DOCUMENTS

| | | | |
|---|---|---|---|
| 4,033,343 A | 7/1977 | Jones | |
| 4,211,221 A | 7/1980 | Schwanbom | |
| 4,487,207 A | 12/1984 | Fitz | |
| 4,519,792 A * | 5/1985 | Dawe ........................... | 604/152 |
| 4,587,967 A | 5/1986 | Chu | |
| 4,617,637 A | 10/1986 | Chu | |
| 4,622,963 A | 11/1986 | Ansite | |
| 4,682,591 A | 7/1987 | Jones | |
| 4,726,366 A | 2/1988 | Apple | |
| 4,823,788 A | 4/1989 | Smith | |
| 4,957,107 A | 9/1990 | Sipin | |
| 4,971,049 A | 11/1990 | Rotariu | |
| 5,107,830 A | 4/1992 | Younes | |
| 5,211,171 A | 5/1993 | Choromokos | |
| 5,289,819 A * | 3/1994 | Kroger et al. ............ | 128/200.24 |
| 5,303,699 A | 4/1994 | Bonassa | |
| 5,493,488 A | 2/1996 | Castle | |
| 5,503,145 A | 4/1996 | Clough | |
| 5,623,921 A | 4/1997 | Kinsinger | |
| 5,666,948 A * | 9/1997 | Matson ..................... | 128/200.23 |
| 5,676,133 A * | 10/1997 | Hickle et al. ............. | 128/205.12 |
| 5,794,986 A | 8/1998 | Gansel et al. | |
| 5,862,802 A | 1/1999 | Bird | |
| 6,000,396 A | 12/1999 | Melker | |
| 6,041,777 A | 3/2000 | Faithfull | |
| 6,131,571 A | 10/2000 | Lampotang et al. | |
| 6,344,160 B1 | 2/2002 | Holtzberg | |
| 6,523,538 B1 | 2/2003 | Wikefeldt | |
| 6,604,523 B2 | 8/2003 | Lurie et al. | |
| 6,609,518 B2 | 8/2003 | Lamb | |
| 7,000,612 B2 | 2/2006 | Jafari et al. | |
| 7,290,542 B1 * | 11/2007 | Carpin ..................... | 128/200.21 |
| 7,314,046 B2 * | 1/2008 | Schroeder et al. ....... | 128/200.14 |
| 7,347,204 B1 | 3/2008 | Lindsey | |
| 7,458,390 B2 | 12/2008 | Gossweiler | |
| 7,604,006 B2 * | 10/2009 | Wolf et al. ............... | 128/203.12 |
| 2002/0104537 A1 | 8/2002 | Banner | |
| 2003/0037786 A1 | 2/2003 | Biondi | |
| 2003/0168062 A1 | 9/2003 | Blythe | |
| 2003/0168066 A1 | 9/2003 | Sallvin | |
| 2004/0173218 A1 * | 9/2004 | Yamada et al. ................. | 128/856 |
| 2004/0206351 A1 * | 10/2004 | McFarland, Jr. .......... | 128/203.12 |
| 2005/0005936 A1 | 1/2005 | Wondka | |
| 2005/0121035 A1 | 6/2005 | Martin | |
| 2005/0205098 A1 | 9/2005 | Lampotang | |
| 2006/0048781 A1 | 3/2006 | Nawata | |
| 2006/0144396 A1 | 7/2006 | DeVries | |
| 2006/0180149 A1 | 8/2006 | Matarasso | |
| 2007/0169776 A1 | 7/2007 | Kepler | |
| 2007/0193579 A1 * | 8/2007 | Duquette et al. ......... | 128/204.18 |
| 2008/0168990 A1 | 7/2008 | Cooke | |
| 2008/0216836 A1 | 9/2008 | Ottestad | |
| 2009/0007912 A1 * | 1/2009 | Lindell et al. ............ | 128/204.18 |
| 2010/0139657 A1 * | 6/2010 | Chalvignac et al. ..... | 128/204.22 |
| 2011/0100372 A1 * | 5/2011 | Betz et al. ................. | 128/206.19 |

OTHER PUBLICATIONS

International Search Report for PCT/US07/081198, Apr. 16, 2008, International Search Authority.

International Search Report for PCT/US10/23792, Jun. 29, 2010, International Search Authority.

International Preliminary Report on Patentability, PCT/US10/23792, Aug. 16, 2011, International Search Authority.

* cited by examiner

VENTILATOR FOR RAPID RESPONSE TO RESPIRATORY DISEASE CONDITIONS

CROSS-REFERENCE

The present invention relies on, U.S. Provisional Patent Application No. 61/151,443, entitled "Ventilator for Rapid Response to Respiratory Disease Conditions" and filed on Feb. 10, 2009, for priority. Further, the present invention is a continuation-in-part of U.S. patent application Ser. No. 11/678,201, of the same title, filed on Feb. 23, 2007 now abandoned, which further relies on U.S. Provisional Patent No. 60/776,493, filed on Feb. 23, 2006 for priority and is a continuation-in-part to U.S. patent application Ser. No. 11/871,341, of the same title, filed on Oct. 12, 2007 now U.S. Pat. No. 8,714,156, which further relies on U.S. Provisional Patent No. 60/829,502, filed on Oct. 13, 2006, for priority. The specifications of all of the aforementioned applications are incorporated herein by reference in their entirety.

FIELD OF THE INVENTION

The present invention relates generally to the field of ventilators, and, more specifically, to a ventilator system that addresses respiratory distress due to the onset of an epidemic or pandemic disease state. More specifically, the present invention is a ventilator system that has control and range of operation so that it meets the needs of ARDS patients in various stages of a compromised state to recovery. In particular, the present invention is a ventilator system that has a mechanical trigger that causes the ventilator to operate in response to spontaneous patient breath. The trigger is preferably a PEEP-referenced spontaneous trigger. In addition, the present invention is a ventilator that includes an alarm system capable of sensing the internal activity of the ventilator and upon sensing an alarm condition will provide a visual and/or audible output.

BACKGROUND OF THE INVENTION

Respiratory distress may be brought on by the onset of an epidemic of an infectious agent in an otherwise healthy population. Respiratory distress can be caused by several disease states, including, but, not limited to Severe Acute Respiratory Syndrome (or "SARS") and Avian Influenza ("Bird Flu"). Severe Acute Respiratory Syndrome (or "SARS"), a serious form of pneumonia resulting in acute respiratory distress and sometimes death, has become an emerging epidemic threat. Every new case of SARS and/or Avian Influenza reported still has the potential to spark another outbreak and even worse, a global pandemic. The most characteristic symptoms of SARS include fever, cough, difficulty breathing and/or other respiratory symptoms. In most cases, supportive care such as the use of supplemental oxygen, chest physiotherapy, and/or mechanical ventilation is needed. Avian Influenza is another emerging epidemic threat that results in severe respiratory distress with an even faster onslaught of symptoms.

Respiratory distress, among other symptoms, includes an impaired ability of the patient to maintain efficient oxygenation. Regardless of the epidemic or infectious agent, however, the respiratory discomfort of critically ill persons that is associated with these disease conditions can be eased, and in many cases recovery hastened, by connecting the patient to a ventilator. Conventionally, to ease impaired respiration, a patient is sedated and mechanically ventilated using either pressure or volume ventilation.

A typical ventilator operates either by forcing pressurized gas (as in a positive-pressure ventilator) into the lungs or by expanding the chest cavity of the patient to draw gas into the lungs (as in a negative-pressure ventilator) under a pre-determined and operator input schedule of gas composition, pressure, and flow pattern.

Currently, conventional ventilators employ microprocessors to control ventilation parameters and to contain pressure and flow measurement transducers, which provide electrical data (via analog-to-digital converters) to the microprocessors for display of monitored parameters and for alarm activation or alert conditions.

In addition, conventional ventilators require either the use large fabrication machinery with a complicated set-up to produce the various metal parts or advanced tooling and moulding processes that are necessary to produce highly durable plastic parts. As new features and ventilating modes are added, the complexity of operation increases as the existing controls and display areas are burdened with the requirement of facilitating input and display of the new features. Thus, conventional ventilators are complex devices and are costly to manufacture and operate.

In addition, conventional ventilator systems are designed to handle a wide range of patient conditions. For example, a patient in the intensive care unit of a hospital typically is overcome by a number of disorders or disease states, in which the body systems are in danger of failing. The intensive care unit must also be able to handle a wide range of patients with a wide range of complaints, including surgery, trauma, heart disease, infection, etc. Thus, conventional ventilators have a large number of operational modes, produced by a complicated set of components, requiring a skilled technician to set up the system.

Because a large number of the United States (and global population) is expected to become ill during a pandemic influenza outbreak, the current healthcare system will rapidly become overwhelmed and patient care may need to be provided by inexperienced healthcare providers with limited or no respiratory support training. Thus, there is a need for domestically manufactured next generation portable fully kitted ventilators to manage an overwhelming number of respiratory compromised patients.

What is also needed is a disaster response protocol for using the rapid response ventilator of the present invention such that it can be used by any entity, including, but not limited to the government, a third party supplier, a hospital, ambulatory services, distributor, non-profit organization, disaster center, or other entities.

Therefore, what is needed is a ventilator that has physical and operational simplicity. What is also needed is a ventilator that is manufactured with materials that are readily available. What is also needed is a ventilator that can be fabricated with simpler, low-cost tooling and methods.

In addition, what is needed is a ventilator that is capable of responding to respiratory distress brought on by an infectious agent in an otherwise healthy population.

What is also needed is a ventilator that is capable of responding to varying patient needs.

What is also needed is a ventilator that is capable of responding to a patient's spontaneous breath without battery, electrical, or other external power. What is also needed is a trigger that can be used to detect and cause the ventilator to respond to a patient's spontaneous breath.

What is also needed is a ventilator that is capable of meeting the needs of the ARDS patient ranging from a critical state until the patient can be safely weaned from the ventilator.

What is also needed is a ventilator that can be manufactured easily and cost effectively at any time the onset of a respiratory epidemic is detected, in scalable volumes.

In addition, what is needed is a ventilator that can be manufactured in any location quickly, prior to the peak period of the epidemic. What is also needed is a ventilator that can ease the burden on ventilator resources in certain communities.

What is also needed is a ventilator that has low power use requirements.

SUMMARY OF THE INVENTION

The present specification discloses a method of manufacturing a ventilator comprising the steps of a) obtaining main housing, wherein the main housing comprises a first housing with internal structures formed to support enclosure of a first component set and a second component set, wherein the first housing further comprises at least one patient connection port; a second housing with internal structures formed to support enclosure of a third component set and a fourth component set, wherein the second housing further comprises an exhaust port; and a third housing with internal structures formed to support enclosure of an alarm printed circuit board (PCB), b) obtaining the first, second, third and fourth component sets, c) obtaining a printed circuit board (PCB) having an alarm circuit, and d) enclosing the first and second component sets in the first housing; the third and fourth component sets in the second housing and the PCB within the third housing.

Optionally, the ventilator is disposable and/or reusable. The first, second, third and fourth component sets are molded using silicone rubber. The main housing, the first, second, third and fourth component sets and the PCB are created using a kit comprising: CAD files defining a plurality of molds for casting the main housing and the first, second, third and fourth component sets; material sources and specifications for the castings, a printed circuit board comprising an alarm circuit; and a lithium battery.

Optionally, the main housing, the first, second, third and fourth component sets, and the PCB are created using a kit comprising: molds for casting the main housing and the first, second, third and fourth component sets; material sources and specifications for the castings, a printed circuit board having an alarm circuit, and a lithium battery. The first, second and third housings are attached using clip-on connectors. The clip-on connectors are integrated into the moldings such that two portions of the components or housing overlap to at least a minimum area and have at least one feature, such as grooves, that engages within the overlapping edges.

The ventilator is tested by applying a pressurized gas to the ventilator; performing a leak test to ensure that the gas supply connections are free of leaks; and performing a functional test to verify operability of the ventilator. The step of applying a pressurized gas to the ventilator comprises connecting a conventional medical device oxygen hose to both a standard threaded male connector formed within the molding and an oxygen supply ranging from 280 kPa to 450 kPa.

The step of performing a leak test comprises pressurizing the ventilator with the outlet occluded or blocked, increasing the oxygen pressure, turning off the oxygen supply, and monitoring the pressure for approximately one minute. The functional test comprises connecting, via a monitoring test fixture, ventilator outlets to a patient circuit and a test lung of C20, R20; applying a gas pressure such that the ventilator begins to run; and comparing displayed parameters to readings on the test fixture. Optionally, a go/no go indicator is employed to ensure product safety.

In another embodiment, the present specification discloses a kit for manufacturing a ventilator comprising: a first housing with internal structures formed to support enclosure of a first component set and a second component set, wherein the first housing further comprises at least one patient connection port; a second housing with internal structures formed to support enclosure of a third component set and a fourth component set, wherein the second housing further comprises an exhaust port; and a third housing with internal structures formed to support enclosure of an alarm printed circuit board (PCB); and a printed circuit board (PCB) having an alarm circuit. Optionally, the kit comprises the first, second, third and fourth component sets. The ventilator is disposable. The first, second, third and fourth component sets are molded using silicone rubber. The kit further comprises CAD files defining a plurality of molds for casting the first, second, third and fourth component sets; material sources and specifications for the castings; and a lithium battery.

BRIEF DESCRIPTION OF THE DRAWINGS

These and other features and advantages of the present invention will be appreciated, as they become better understood by reference to the following detailed description when considered in connection with the accompanying drawings, wherein:

FIG. 8b is a graph depicting a typical ventilation cycle of pressure against time and further depicts operation of the plurality of valves of the device shown in FIG. 8a;

FIG. 8c illustrates a first stage operation of the valves shown in FIG. 8a;

FIG. 8d illustrates a second stage operation of the valves shown in FIG. 8a;

FIG. 8e illustrates a third stage operation of the valves shown in FIG. 8a;

DETAILED DESCRIPTION OF THE INVENTION

Figure 1:
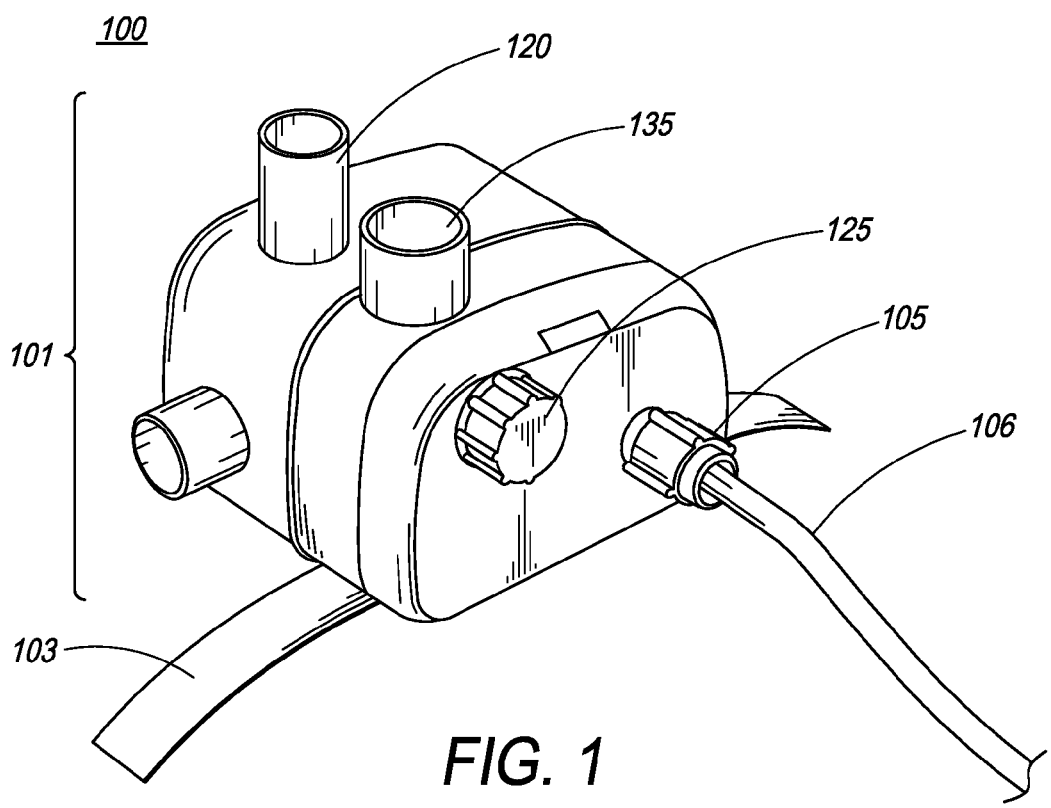
FIG. 1 is an illustration of a first embodiment of the ventilator of the present invention.

The present invention is directed towards a ventilator system that can be manufactured quickly with minimal skill requirements and rapidly deployed in response to epidemic respiratory disease conditions.

The present invention is directed towards multiple embodiments. Language used in this specification should not be interpreted as a general disavowal of any one specific embodiment or used to limit the claims beyond the meaning of the terms used therein. Reference will now be made in detail to specific embodiments of the invention. While the invention will be described in conjunction with specific embodiments, it is not intended to limit the invention to one embodiment.

In one embodiment, the present invention is directed towards a ventilator having a minimal number of controls. In one embodiment, the present invention is directed towards a ventilator that is used to give ventilation or mechanical breathing to a patient suffering ARDS. In one embodiment, the mechanical ventilation of the present invention is based on pressure control and has variable pressure, breathing rate, and oxygenation.

Preferably, the ventilator is rapidly deployable. Still preferably, the ventilator is as easy and intuitive to operate as possible. Still preferably, the ventilator is capable of sustaining at least 75% of epidemic respiratory distress victims who require assisted ventilation until resuming normal breathing.

In another embodiment, the present invention is directed towards a simple, safe and effective means for delivering oxygen-enriched air to the ventilator when the ventilator is used in emergency and overflow facilities outside the standard hospital environment.

In another embodiment, the present invention is directed towards a rapid response ventilator system that further provides for the use of or can accommodate the use of a heat and moisture exchanger (HME) or humidifying filter for trapping moisture and heat for patients on an extended use. It should be understood by those of ordinary skill in the art that any commercially available HME can be employed.

In another embodiment, the present invention is directed towards a rapid response ventilator system that is capable of being manufactured and distributed in sufficient volume and at very low cost in a substantial part of the world.

In yet another embodiment, the present invention is directed towards a rapid response ventilator system that can be safely and responsibly disposed of after use.

The present invention is also directed towards a ventilator that has physical and operational simplicity. In addition, the present invention is directed towards a ventilator, which, in one embodiment, is manufactured with materials that are readily available. In other embodiments, the ventilator of the present invention can be fabricated with simple, low-cost tooling and methods.

In one embodiment, the ventilator of the present invention is a simple, moulded device that requires little or no adjustment. The simple, no adjustment moulded device is advantageous in that it poses no additional risk to the patient. In one embodiment, the ventilator of the present invention has limited controls.

In another embodiment, the ventilator of the present invention is ruggedized and can be used in varying environments. In one embodiment, ruggedization includes determining area of usage and selecting an appropriate material based on various characteristics, including thickness, availability, durability, malleability/moldability, and performance in use. It should be understood by those of ordinary skill in the art that the selection of material is dependent on the environment of use.

In one embodiment, the ventilator of the present invention is adequately shielded for radio frequency interference (RFI), electromagnetic interference (EMI) and conductive interference, such as a power surge.

In one embodiment, the ventilator of the present invention is manufactured using pre-fabricated tooling for storage at strategic manufacturing sites.

In one embodiment, the ventilator of the present invention is manufactured using tooling fabricated from less durable material at the onset of an epidemic. In one embodiment, the fabrication material includes, but is not limited to, aluminum. It should be understood by those of ordinary skill in the art that any number of tooling materials and tooling kit manufacturing processes may be used in the present invention, including, but, not limited to, bronze sintering and steel fabrication. In one embodiment, the choice of tooling material and kit fabrication selected depends upon the needs of the population and the epidemic and/or pandemic situation. For example, but, not limited to such example, the volume of devices needed may be an indicator of which materials should be used for the tooling and the tooling kit processes.

In one embodiment, the ventilator of the present invention is manufactured using parts that are fabricated in an automated system. Thus, in this embodiment, no tooling is actually created.

In one embodiment, the ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel.

In one embodiment, the ventilator of the present invention is manufactured using tooling fabricated from a material of lower durability than steel at the onset of an epidemic. In one embodiment, the material of lower durability is aluminum. Preferably, the materials are readily accessible to produce a more limited number of units for more localized outbreaks of disease and the tooling is designed such that it can be manufactured fairly rapidly.

In one embodiment, the ventilator of the present invention is manufactured using parts that are fabricated in an automated system directly from design documentation. Thus, no tooling is actually created. This embodiment is particularly useful for supporting remote areas where the ultimate goal is to transport patients to larger centres while still providing temporary respiratory support. Advantageously, in this embodiment, the manufacturing method allows for the ventilators of the present invention to be produced on demand without the time it takes to manufacture the tooling.

In each of the manufacturing embodiments described above, assembly is simple and does not require highly specialized skills or training. The ventilator can thus be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded or disrupted.

In one embodiment, the ventilator of the present invention is operable in a plurality of modes, including adult, pediatric, and infant. In one embodiment, an operator selects a mode by adjusting the inspired gas flow rate, thus affecting the inspiratory time, or the time to reach the pre-set maximum pressure.

In one embodiment, the maximum pressure is pre-set by the operator. In one embodiment, the ventilator is operated at a maximum pressure suitable for most patients without causing any patient injury. In one embodiment, the ventilator operates in a pressure range of 10 cm $H_2O$ to 70 cm $H_2O$. In another embodiment, the ventilator can provide pressure-controlled ventilation up to a pre-set pressure of 20 cm $H_2O$. In another embodiment, the ventilator can provide pressure-controlled ventilation up to a pre-set pressure of 25 cm $H_2O$. In yet another embodiment, the ventilator can optionally provide a venturi to give at least 60% oxygen. It should be noted here that any number of distinct pressures may be set by the operator depending upon individual patient assessment and/or need.

In another embodiment, the ventilator of the present invention is capable of responding to patient need. More specifically, in one embodiment, if a patient begins to resume breathing spontaneously, the ventilator of the present invention is capable of entering a passive mode. In another embodiment, if a patient fails to maintain spontaneous unassisted breath, the ventilator begins to operate and assist with oxygen delivery to the patient.

In one embodiment the present invention is directed towards a disposable ventilator. In another embodiment, the present invention is a limited use system wherein the limitations of use may include one of a plurality of limitations, including singular patient use, run-time, or calendar time. In one embodiment, the present invention is a single patient-use, disposable ventilator with no specific life span.

In one embodiment, the present invention is a kit for a disposable ventilator, including a sealed packaging including the disposable ventilator, and a disposable bag into which the disposable ventilator may be inserted after use with a single patient.

In one embodiment, the ventilator of the present invention is lightweight and transportable, so that it can be stored and deployed easily. In one embodiment, the rapid response ventilator of the present invention weighs substantially less than standard, conventional electronic ventilators, both portable and stationary, which tend to weigh, on average 30 pounds or more. In one embodiment, the ventilator of the present invention weighs less than 15 total pounds. In another embodiment, the ventilator of the present invention weighs in the range of 2 pounds to 5 pounds.

Persons of ordinary skill in the art should note that the ventilator of the present invention is distinguishable from a resuscitator. A resuscitator is designed to provide air or oxygen to patient who has healthy lungs while being transported from an accident site to an emergency room. The patient may not be breathing and he is made to breath if the lungs are not compromised (fairly short period of time, like an ambu-bag). However, a ventilator takes over the breathing function for a patient who has compromised lungs. It is an automated mechanism that supports life.

FIG. 1 is an illustration of a first embodiment of the ventilator of the present invention. In one embodiment, ventilator 100 comprises main housing 101 for housing ventilator components. In one embodiment, ventilator 100 is disposable. In another embodiment, ventilator device 100 is intended for single patient use. In yet another embodiment, ventilator 100 is intended for multiple-patient use, and thus, can be re-used. Preferably, ventilator devices intended for re-use are designed and manufactured such that they can be easily dismantled and cleaned.

In another embodiment, ventilator 100 is manufactured using materials that can be sterilized at a preferred sterilization temperature of 138° C., or the standard temperature of an autoclave. These materials include high temperature plastics, which require more advanced tooling. In one multiple-use embodiment, the ventilator is fabricated with a plastic material with a low melting point, thus allowing its manufacture with cost effective tooling.

In one embodiment, the rapid response ventilator of the present invention is manufactured with connectable parts. The connectable parts of the ventilator can be attached by various methods, either fixedly or removably, such as but not limited to gluing, screwing, or welding, or any other suitable means of connecting tooling parts as are well known to those of ordinary skill in the art.

Ventilator 100 further comprises flow control valve or breathing rate control knob 125, alarm/battery activation tag 103, at least one patient interface or connection port 120, and gas supply connection port 105 that connects to a gas source [not shown] through hose 106.

In one embodiment of the ventilator of the present invention, the breathing rate control knob 125 is the only control that is required to be adjusted by the operator. The breathing rate control knob 125 can be adjusted to allow for various modes of operation, including but not limited to adult mode, pediatric mode, and infant mode. As described above, an operator selects a mode by adjusting the inspired gas flow rate, thus affecting the inspiratory time, or the time to reach the pre-set maximum pressure.

Referring back to FIG. 1, to begin using the rapid response ventilator 100 of the present invention, the operator must first remove the ventilator from its packaging, which is preferably sterile. In one embodiment, the ventilator 100 is then mounted in a safe and stable position located above, but proximate to the patient. The operator then removes the alarm activation tag 103 from the battery of the ventilator by pulling as indicated.

In one embodiment, once the ventilator is unpackaged and positioned, the operator, or any other qualified and trained personnel, sedates and intubates the patient. The ventilator 100 is then connected to the patient's endotracheal tube using a standard breathing circuit and, optionally, a humidifying filter (not shown) at the patient connection point 120. In another embodiment, ventilator 100 is connected to the patient via a breathing mask assembly at patient connection point 120. In yet another embodiment, ventilator 100 is connected to the patient via a laryngeal mask airway (LMA) device. The various patient connection devices for delivering oxygen to the patient are described in greater detail below with respect to FIGS. 3 and 5.

The operator then sets the ventilation control via the breathing rate control knob 125. Preferably, the patient's physical dimensions, such as but not limited to height and weight, are employed to determine the breathing rate. The oxygen supply hose 106, connected at gas supply port 105 is then connected to an oxygen source (not shown) to enable ventilator operation.

Ventilator 100 also comprises exhaust port 135, the operation of which is described in greater detail below with respect to FIG. 3. In one embodiment, the ventilator is powered by compressed oxygen source operating at a pressure ranging from 40 PSI to 70 PSI. In another embodiment, the oxygen source operates at a pressure ranging from 5 to 60 PSI. Preferably, though optionally, this drives all mechanical functions of the system. The Positive End-Expiratory Pressure (hereinafter "PEEP") control is then set as indicated by the patient's oxygenation indications. PEEP refers to the residual positive pressure that remains in the airway at the end of the expiratory cycle. It is employed to prevent the lung from fully collapsing after each breath, thus improving gas exchange in the lung.

Ventilation is continued with frequent observation of alarm status (described below) and patient oxygenation. In one embodiment, when ventilation is complete or discontinued, the ventilator and breathing circuit components are sealed in a disposable bag and taken to the nearest disposal collection point for proper disposal. In another embodiment, when ventilation is complete or discontinued, the ventilator and breathing circuit components are appropriately sterilized and re-packaged for subsequent use, as described above.

Figure 2:
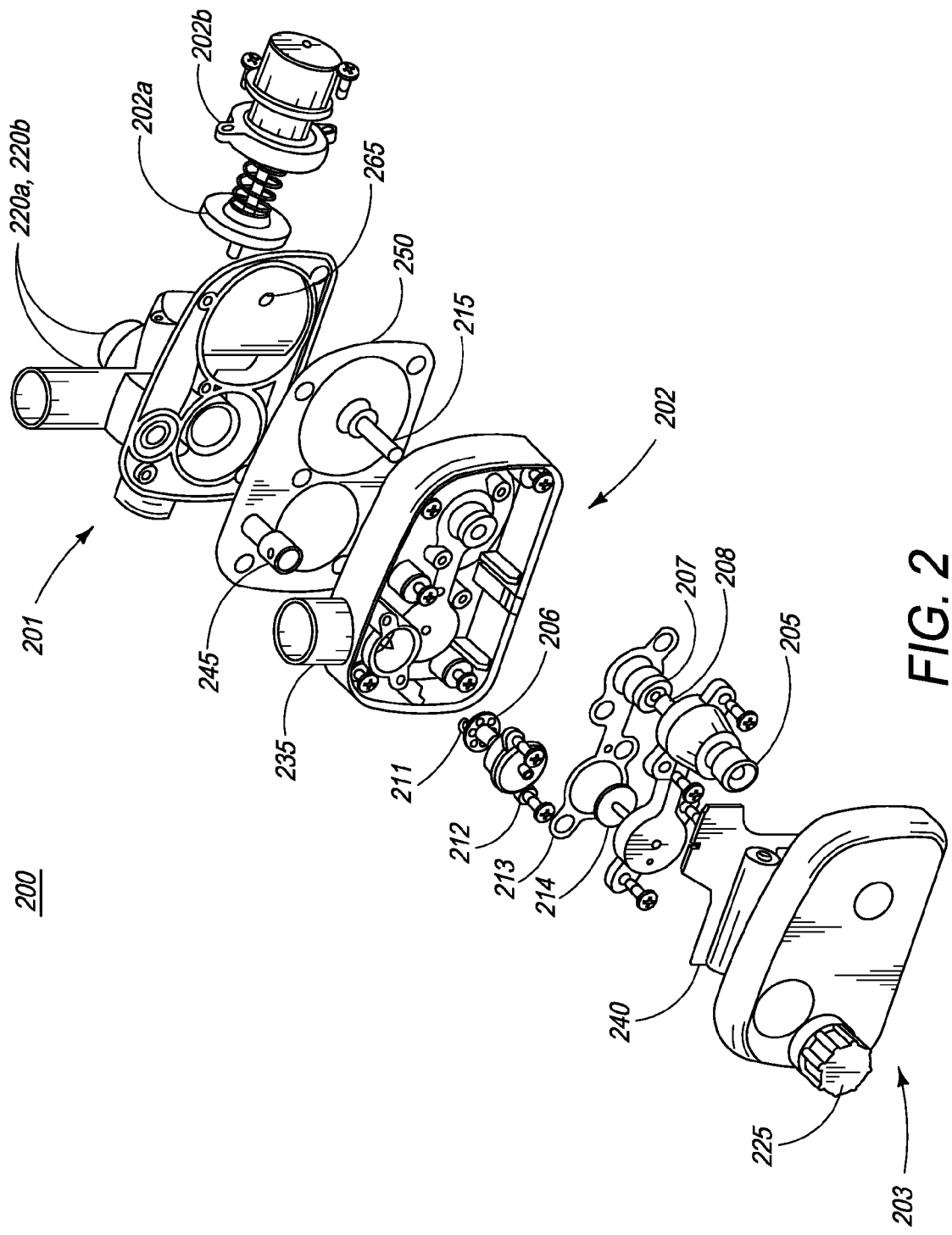
FIG. 2 is a schematic diagram of the system components of a first embodiment of the ventilator of the present invention.

FIG. 2 is a detailed illustration of the system components of a first embodiment of the ventilator of the present invention. In one embodiment, ventilator 200 comprises patient interface or connection port 220, gas over-pressure relief valve 202a and valve cover 202b, leak jet 265, first diaphragm actuator 250, actuator path or inhalation conduit 215, jet disc 206, bellows seal 207, first seal 208, compressed gas interface 205, branch conduit 245, "O"-ring 211, first jet cover 212, top cover seal 213, electronics actuator 214, printed circuit board (PCB) 240, breathing rate control knob 225, and exhaust port 235. In an optional embodiment, ventilator 200 further comprises a venturi (not shown).

In one embodiment, patient interface 220 further comprises patient interface 220a for accepting air from the patient and patient interface 220b for delivering oxygen to the patient.

Figure 3:
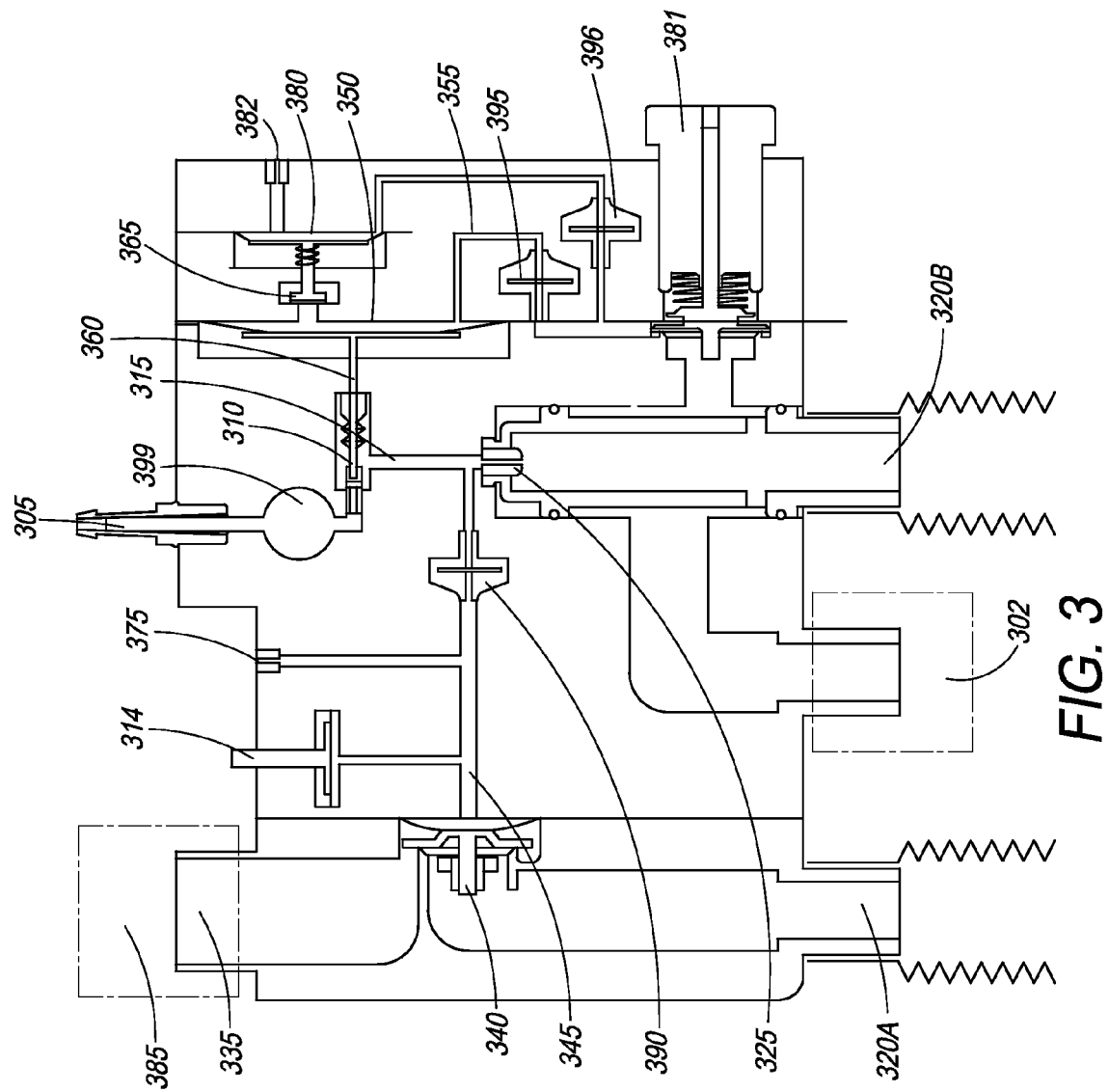
FIG. 3 is a schematic diagram of a first embodiment of the ventilator of the present invention.

The operational characteristics of the system components of FIG. 2 are described in detail with respect to FIG. 3. In addition, alarm circuit PCB 240, which in one embodiment is operably connected to the ventilator of the present invention via electronics actuator 214, is discussed in detail with respect to FIG. 4 below.

FIG. 3 is a schematic diagram of a first embodiment of the ventilator of the present invention. The operational characteristics of the first embodiment of the rapid response ventilator of the present invention will be described with respect to the schematic diagram of FIG. 3. It should be noted again that the operational descriptions below is exemplary and that language used in this specification should not be interpreted as a general disavowal of any one specific embodiment.

Referring now to FIG. 3, ventilator 300 comprises a compressed gas interface 305, which further comprises a compressed gas reservoir 399, which in use, is connected to a pressurized gas source (not shown). In one embodiment, the pressurized gas is oxygen. In another embodiment, the pressurized gas is medical compressed air. In one embodiment, compressed gas interface 305 is an inlet port.

Ventilator 300 further comprises gas control valve 310. Gas control valve 310 is connected to compressed gas reservoir 399 on one end. At the other end, gas control valve 310 is connected to inhalation conduit 315. Inhalation conduit 315 is operationally connected to patient interface 320 via flow control valve 325. In one embodiment, flow control valve 325 is a knob, capable of being manipulated to control breath rate. In another embodiment, flow control valve 325 is a fixed jet, delivering a breathing rate proportional to patient size.

In one embodiment, patient interface further comprises patient interface 320a for accepting air from the patient and patient interface 320b for delivering oxygen to the patient.

In one embodiment, patient interfaces 320a and 320b is connected to a breathing mask. In another embodiment, patient interfaces 320a and 320b are connected to an endotracheal tube. In yet another embodiment, patient interfaces 320a and 320b are connected to a laryngeal mask airway (LMA) device. Laryngeal mask airway devices are well-known to those of ordinary skill in the art and are used in anesthesia and emergency medicine for airway management. More specifically, it is a tube with an inflatable cuff that is inserted into the pharynx. It causes less pain and coughing than an endotracheal tube, and is easier to insert. It should be noted, however, that the laryngeal airway mask is not recommended for anyone at risk for lung aspiration.

In another embodiment, the breathing circuit is equipped with universal connectors for gas input and output and patient input and output.

Inhalation conduit 315, which is proximate to 320b, extends from patient interface 320b into an exhalation interface, which comprises exhaust port 335. Exhaust port 335 is controlled by expiratory valve 340, in communication with branch conduit 345 and connected to inhalation conduit 315, which is proximate to gas control valve 310. In one embodiment, a PEEP control mechanism is connected to expiratory valve 340. The PEEP control is then set, using external PEEP valve 385, as indicated by the patient's oxygenation indications.

In one embodiment, the ventilator of the present invention also comprises a pressure detector 314. In one embodiment, pressure detector 314 is employed as an interface to the alarm system described in FIG. 4. In one embodiment, pressure detector 314 is an electronic diaphragm actuator that translates activity within the ventilator into a signal that can be used to alarm the operator upon pre-determined events, as described in further detail below.

Diaphragm actuator 350 is connected to patient interface 320b via conduit 355 and non-return valve 395. Diaphragm actuator 350 is sealed to gas control valve 310, with push rod 360. Diaphragm actuator 350 can be sealed to gas control valve by any sealing means known to those of ordinary skill in the art, including, but, not limited to lip-sealing. Push rod 360 actuates the gas control valve 310 in response to the movement of diaphragm actuator 350. Diaphragm actuator 350 is also equipped with a servo valve 365, which is described in greater detail below.

In operation, a compressed gas is supplied to ventilator 300 from a source, such as a tank, preferably at a pressure greater than 5 PSI. In one embodiment, the compressed gas is oxygen. A gas regulator (not shown) regulates the delivery of compressed gas at a suitable pressure for use within the ventilator unit 300. In one embodiment, a suitable pressure for the compressed gas supply is in the range of 5 PSI to 60 PSI. In one embodiment, a suitable pressure for the compressed gas supply is 50 PSI. In another embodiment, a suitable pressure for the compressed gas supply is 30 PSI.

Inhalation is enabled by delivering regulated oxygen through gas control valve 310 and through inhalation conduit 315 and to flow control valve 325, thus increasing the pressure in inhalation conduit 315. The resultant back pressure in inhalation conduit 315, caused by flow control valve 325, is passed, via non return valve 390 to branch conduit 345, which subsequently actuates the expiratory valve 340. Once actuated, expiratory valve 340 seals exhaust port 335, enabling oxygen delivery to the patient and resulting in a pressure increase.

Diaphragm actuator 350 senses the resultant increase in pressure via non-return valve 395 and conduit 355 and causes push rod 360 to move up until gas control valve 310 is actuated, and thus closed, and gas flow is subsequently halted.

The pressure within diaphragm actuator 350 is retained by a servo valve 365. Servo valve 365 is controlled via servo diaphragm actuator 380. In particular, leak jet 382 reduces the pressure within servo diaphragm actuator 380 until the gas control valve 310 opens. When gas control valve 310 opens, servo valve 365 opens and subsequently discharges the gas pressure holding diaphragm actuator 350 in position, thus halting gas flow via flow control valve 325. When servo valve 365 is closed, oxygen flow resumes to the patient, thus repeating the cycle.

The initial back pressure responsible for closing expiratory valve 340 equalizes across flow control valve 325. The back pressure decays via leak jet 375, which controls the inspiration time, thus allowing expiratory valve 340 to open to the atmosphere. Exhalation is spontaneous when the over-pressure stored in the lungs during inhalation is released. The over-pressure in the lungs of the patient discharges through exhaust port 335, in the form of gas flow. In addition, leak jet 382 sets the expiratory time. Thus, the action of leak jets 375 and 382 set the breathing rate and therefore, the inhalation to exhalation ratio.

Referring back to FIG. 3, in one embodiment of the ventilator of the present invention, the expiratory time is preset to at least 1.5 seconds via adjusting the size of leak jet 382 and by adjusting the internal volume of servo diaphragm 380. In one embodiment, the expiratory time is preset to 2 seconds. In one embodiment of the ventilator of the present invention, the breathing rate is set in a range of between 10 and 45 Breaths per Minute (BPM). In another embodiment of the ventilator of the present invention, the breathing rate is set in a range of between 4 to 40 BPM (±10%).

In one embodiment of the present invention, the flow control valve or breathing rate control knob 325 is the only control that is required to be adjusted by the operator. The breathing rate control knob 325 can be adjusted to allow for various modes of operation, including but not limited to adult mode, pediatric mode, and infant mode.

In one embodiment, the ventilator of the present invention operates in Pressure Control Mode. In one embodiment of the present invention, airway pressure control 381, located proximate to patient interface 320b, is employed to set the target patient pressure in the control system. In one embodiment, the ventilation pressure is fixed and set by dimensions of diaphragm actuator 350 and the available settings of the regulator. In one embodiment, the pressure is suitable for most patients without causing any patient injury. In one embodiment, the ventilation pressure is variable and set by the operator. In one embodiment, the ventilator 300 operates in a range of 10 cm $H_2O$ to 70 cm $H_2O$. In another embodiment, ventilator 300 operates in a range of 20 cm $H_2O$ to 35 cm $H_2O$. In one embodiment, the ventilator 300 operates at a maximum of 20 cm $H_2O$. In another embodiment, the ventilator 300 can provide pressure-controlled ventilation at a pre-set pressure of 25 cm $H_2O$. Pressure relief valve 302 is located in the circuit to the patient that is set to ensure that over-pressure is not delivered to the patient.

In one embodiment, the ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel using conventional tool room processes evident to persons of ordinary skill in the art. In another embodiment, the tool-set is fabricated using conventional Direct Metal Laser-Sintering process that enables rapid tool production in less than 24 hours producing more than 500 parts.

In one embodiment, the ventilator of the present invention is manufactured using tooling fabricated from a material of lower durability than steel at the onset of an epidemic. In one embodiment, the material of lower durability is aluminum. Preferably, the materials are readily accessible to produce a more limited number of units for more localized outbreaks of disease. The tooling can be manufactured fairly rapidly.

In one embodiment, the ventilator of the present invention is manufactured using parts that are fabricated in an automated system directly from design documentation. Thus, in this embodiment, no tooling is actually created. This embodiment is particularly useful for supporting remote areas where the ultimate goal is to transport patients to larger centers but temporary respiratory support is nevertheless required. Advantageously, the manufacturing method of the present invention allows for the ventilators to be produced on demand without the time it takes to manufacture the tooling.

In each of the manufacturing embodiments described above, assembly is simple and does not require highly specialized skills or training.

The ventilator can be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded.

In one embodiment of the rapid response ventilator of the present invention, the ventilator is capable of operating independent of electrical supplies.

In another embodiment, the rapid response ventilator is powered by pressurized oxygen at a regulated pressure.

In another embodiment the rapid response ventilator of the present invention is battery-operated.

In one embodiment, the rapid response ventilator of the present invention further comprises an alarm system.

In one embodiment, the rapid response ventilator of the present invention has an audio and/or visual alarm that alerts upon battery failure, or when the battery voltage falls below an acceptable pre-determined level. Thus, in one embodiment, the electronics of the alarm system are powered by a battery, such as a manganese-alkaline battery, a mercury type battery or any other suitable battery known to persons of ordinary skill in the art. When the battery voltage reaches a pre-determined, factory set voltage level a visual alarm is activated, such as the L.E.D. will start flashing in RED. Optionally, the alarm will also emit an audible alarm, such as a clicking sound. This is indicative that the battery needs to be changed. In one embodiment, the low battery voltage condition is set to sense when the battery voltage is less then 2.5 volts.

In one embodiment, the rapid response ventilator uses universally available standard, over the shelf batteries. In one embodiment, the rapid response ventilator of the present invention employs AA, AAA, C or D batteries. It should be noted that the battery is added upon preparing the device for use, and would not be replaced while the ventilator is on continuous use for a patient. In another embodiment, any standard rechargeable battery may be employed. It should be noted herein that the battery is only, in one embodiment, employed to power the alarms. The ventilator will operate without the batteries installed. Thus, the ventilator of the present invention does not require batteries or electricity to power a control system or interface.

The alarm system of the rapid response ventilator of the present invention is also capable of sensing the internal activity of the ventilator and upon sensing an alarm condition will provide a visual and/or audible output. In one embodiment, an alarm condition is low supply gas pressure. In another embodiment, an alarm condition is disconnection from the patient. In yet another embodiment, an alarm condition is failure to ventilate.

Thus, the alarm system is used to provide an audible and/or visual apnea alarm. In one embodiment, the alarm system causes an L.E.D. to emit a short flash, preferably green, with each breath to confirm that the ventilator system of the present invention is fitted and working properly. If no breaths are detected within a pre-determined time period, an audible and pulsating beep is emitted in conjunction with a flashing L.E.D., preferably RED, to identify that the alarm system of the ventilator of the present invention is in an alarm state. In one embodiment, the pre-determined time period between breath detection is factory pre-set and in the range of 15 to 20 seconds.

Figure 4:
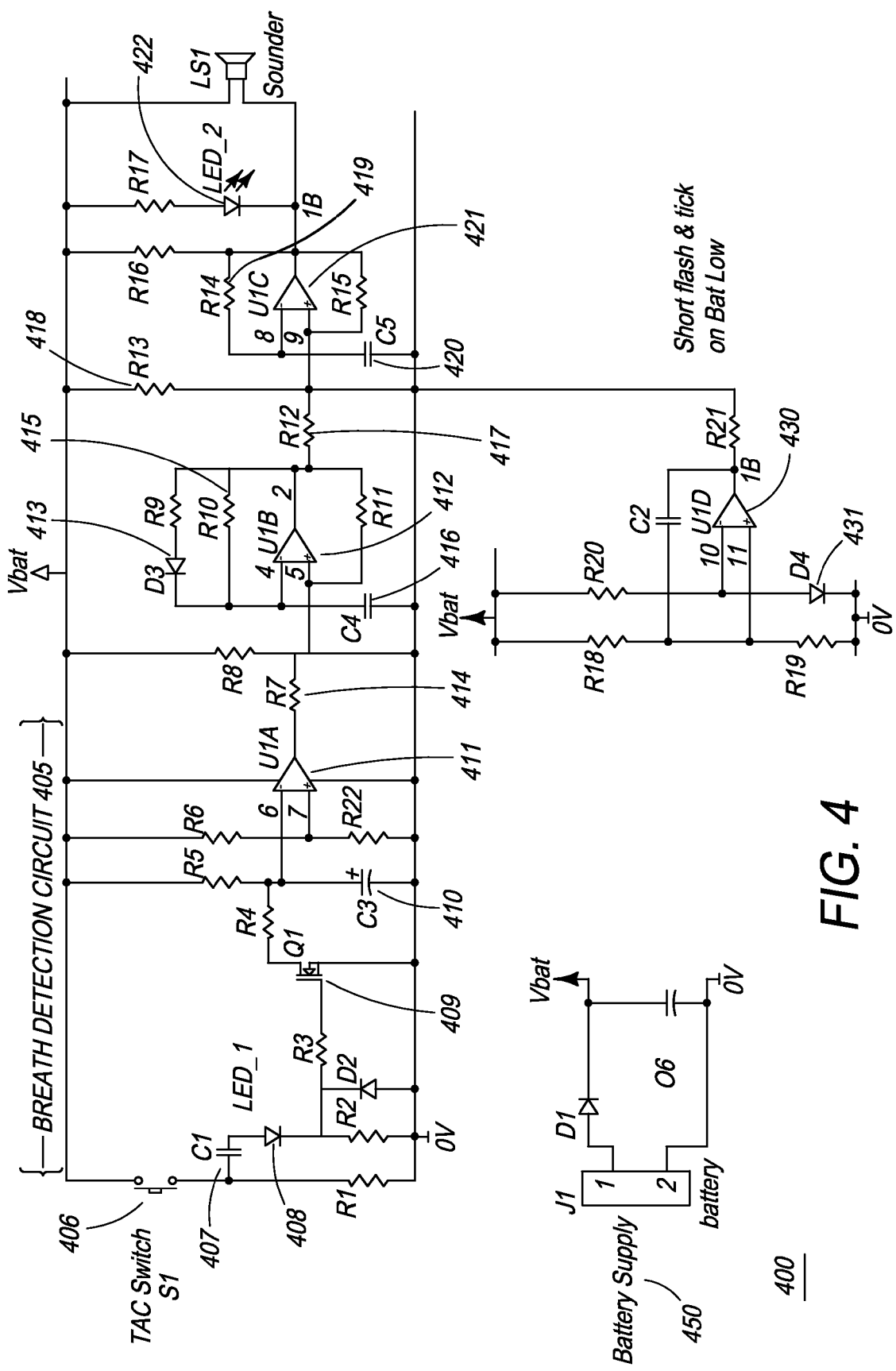
FIG. 4 is a schematic circuit diagram of one embodiment of an alarm circuit that is used in the ventilator of the present invention.

In one embodiment, as described above with respect to FIG. 3 and referring back to FIG. 3, the alarm system is operably connected to the ventilator of the present invention via an electronic diaphragm actuator 314. Specifically, the diaphragm actuator 314 is operably connected to a PCB (not shown), via a plunger on the electronics diaphragm actuator, which moves once per breath under the pneumatic action of the ventilator, and thus initiates sensing activity of the alarm system. The PCB also provides support for the power/battery components via connection to the battery terminals, as shown in FIG. 4. In addition, the audible alarm and LEDs are aligned with the ventilator system of the present invention to allow the sound and light to pass through such that they can operate as visible and audible alerts to the operator. In one embodiment, a change in pressure is detected by the diaphragm actuator which translates activity within the ventilator, into a signal that can be used by the PCB to alarm a pre-determined event, such as displacement of the diaphragm under pressure due to an increase in pressure.

In one embodiment, upon inhalation of the first breath by the patient, the battery supplies power to the alarm system so that it is deployed and thus, the alarm is ready to detect an alarm condition automatically on the occurrence of the first breath, minimizing the risk of an operator forgetting to deploy the alarm. Subsequent breaths alternate between inspiration during which air is supplied by the ventilator to the patient's lungs and expiration during which air passes out of the exhalation valve.

FIG. 4 is a schematic circuit diagram of one embodiment of the alarm circuit (PCB) as employed in the ventilator of the present invention. Referring back to FIG. 2, PCB 240 is employed to provide an alarm circuit to the ventilator system of the present invention. Referring now to FIG. 4, alarm circuit 400 is preferably formed on a printed circuit board that houses the electronic components. In one embodiment, alarm circuit 400 further comprises first stage breath detection circuit portion 405, which further comprises TAC Push Button Switch or membrane 406, which is actuated by the plunger of the electronics actuator (not shown), described with respect to FIG. 3. The plunger of the electronics actuator moves once per breath and thus, once per breath either "opens" or "closes" the TAC Switch 406, depending on orientation of the plunger.

In a first stage of the alarm circuit, when TAC Switch 406 closed and thus actuated, a pulse of current is passed through the circuit, via capacitor 407, and to LED 408 to generate the short confirming flash, described above. The flash decays as the capacitor 407 charges to minimize battery consumption. The peak current is set to provide a wetting effect for the contacts of switch 406. The transient current is detected by gate 409, which then switches on to discharge capacitor 410. If switch 406 does not close, or actuate, and thus remains open, then capacitor 410 will charge until the voltage on the negative input terminal of comparator 411 exceeds the voltage on the positive input terminal comparator 411. Subsequently, the open drain output pin 1 of comparator 411 switches to indicate and alarm condition. In one embodiment, comparator 411 is a dedicated voltage comparator chip.

The second stage of the alarm circuit 400 is an asymmetric oscillator. This oscillation signal provides the on-off modulation for the audible alarm, thus eliminating the need for the operator to distinguish the source of noise, especially in challenging and high background noise environments. When pin 1 of comparator 411 is low, the circuit thus oscillates to generate approximately pulses. The duty cycle and period is set by the values of resistors 414, 415 and capacitor 416. The duty cycle and period are factory set and may be adjusted if different periods and duty cycles are required. In one embodiment, the circuit oscillates to generate 100 msec pulses every 250 msec.

The third stage of alarm circuit 400 is an oscillator, which is, in one embodiment, fixed in the range of between 400 Hz and 1 kHz and provides the LED output upon alarm condition. When pin 2 of comparator 412 is low, the junction of resistors 417, 418 is brought to mid-rail and the oscillator is enabled. The nominal frequency is determined by the time constant of resistor 419 and capacitor 420. When the output of comparator 421 is low, the LED 422 flashes RED and the audible alarm is resonated at the nominal alarm frequency. The output from comparator 421 may, in one embodiment, be buffered if higher drive currents are needed by the particular audible alarm employed.

As mentioned above, alarm circuit 400 is also employed to monitor the battery voltage of battery 450. In one embodiment, comparator 430 is used to monitor the battery voltage against reference diode 431. If the divided voltage falls below the value of reference diode 431, then pin 12 of comparator 430 becomes low and enables the output oscillator described above. The output oscillator enables the short pulsing duration that causes the alarm to emit a periodic clicking noise to warn that the battery supply needs to be replaced.

The alarm system of the rapid response ventilator of the present invention is, in one embodiment, simple to manufacture and requires no calibration.

In one embodiment, the ventilator of the present invention can be operated for the expected duration of the peak of an epidemic.

In another embodiment, the ventilator of the present invention is single-patient use, preferably until the patient is weaned off the ventilator and is breathing independently.

In another embodiment, the ventilator is made of "green" materials and can be easily disposed of when it has been used on a single patient or when an epidemic has passed.

In a second embodiment, the present invention is a ventilator system that has control and range of operation so that it meets the needs of ARDS patients in various stages of a compromised state to recovery.

In addition, the present invention, in a second embodiment, is directed towards a ventilator that is capable of responding to varying patient needs quickly and effectively.

In addition, the present invention is directed towards a ventilator that is capable of meeting the needs of the ARDS patient ranging from a critical state until the patient can be safely weaned from the ventilator. In one embodiment, the ventilator of the present invention is suitable for ARDS patients with a lung compliance range of:

a. Adult C10 to C90
b. Pediatric C5 to C50

Most patients suffering from respiratory failure in a pandemic setting will meet the criteria for acute lung injury (ALI) or acute respiratory distress syndrome (ARDS). Current patient guidelines support the use of low tidal volumes (approximately 6 cc/kg ideal body weight) and the limitation of inspiratory plateau pressure (typically less than 30 cm $H_2O$) while maintaining adequate oxygenation, defined as arterial oxygen saturation of equal to or greater than 93%. Adequate oxygenation is provided by titration of supplemental inspired oxygen and PEEP.

In addition it is important to provide adequate minute ventilation by controlling arterial $PCO_2$, as assessed by an arterial pH of 7.3 to 7.4. Minute ventilation is the product of tidal volume and rate.

Figure 5:
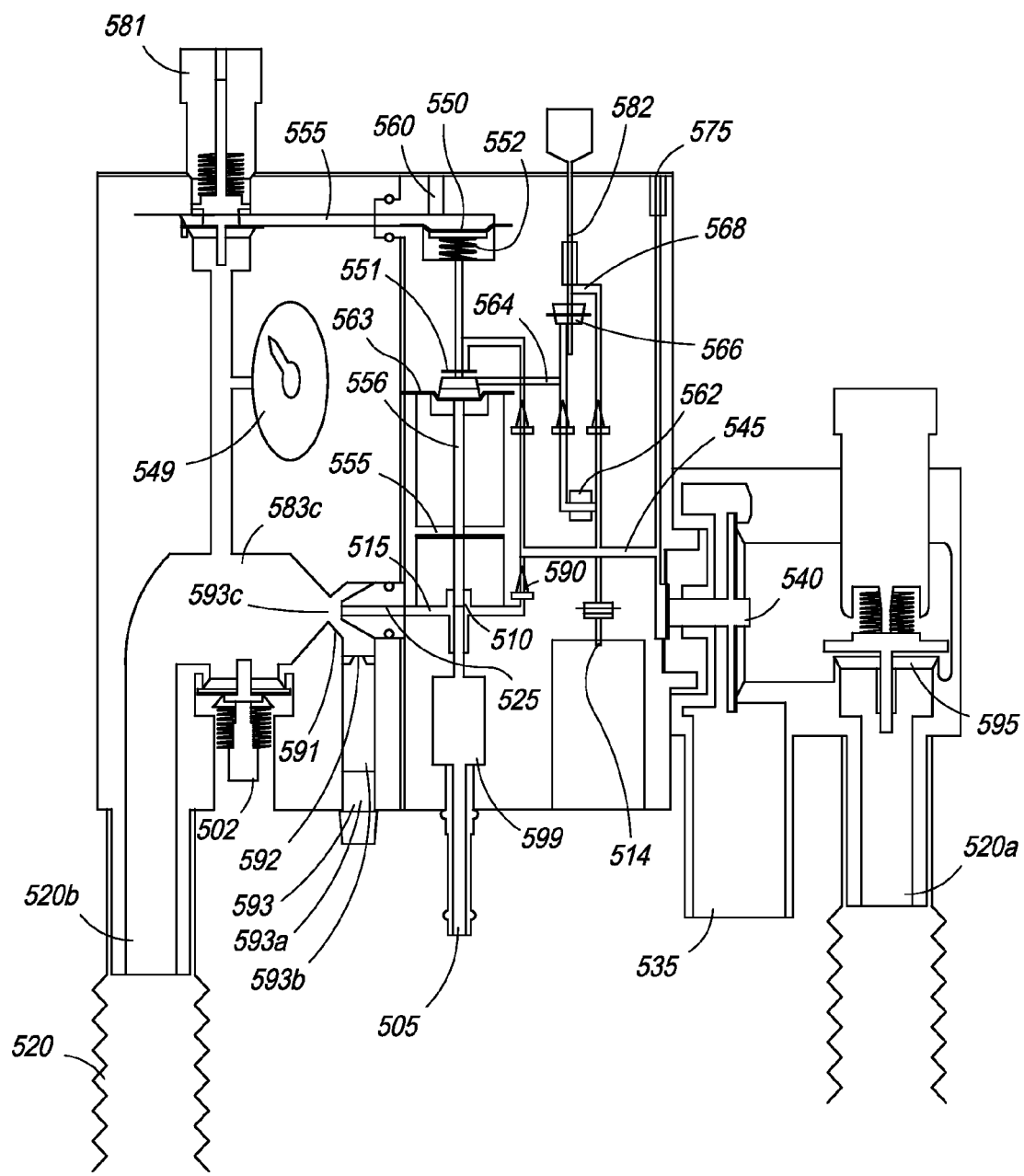
FIG. 5 is a schematic diagram of a second embodiment of the ventilator of the present invention.

In an example of use of the second embodiment of the present invention, as shown in FIG. 5, a very ill patient may present with very severe hypoxemia, thus necessitating the use of high inspired oxygen levels. In one embodiment, the high inspired oxygen level is denoted by $F_iO_2=1.0$, meaning that the percentage of oxygen in the inspired air is 100%. $F_iO_2$ represents the fraction of inspired oxygen, and ranges from 0 to 1.0.

To allow effective oxygen transfer at an $F_iO_2 \le 1.0$ to minimize the risk of toxicity of oxygen, PEEP is added at a rate 5 cm $H_2O$, increasing in 5 cm increments up to a maximum of 15 cm $H_2O$. PEEP allows for the reduction of $F_iO_2$ while maintaining arterial oxygen saturation above 92%. As mentioned above, PEEP refers to the residual positive pressure that remains in the airway at the end of the expiratory cycle. It is employed to prevent the lung from fully collapsing after each breath, thus improving gas exchange in the lung.

Because the patient is very ill, he will likely have non-compliant (or stiff) lungs. Thus, the patient will initially require a high inspiratory pressure to achieve high tidal volumes, which in one embodiment, ranges from 30-35 cm $H_2O$. If the tidal volumes are small enough, the corresponding respiratory rate may be fairly high (25-30/min) to ensure adequate minute ventilation and carbon dioxide excretion. As the patient is improving, however, their lung compliance will increase, and the inspiratory pressure will need to be reduced (in the range of 10-15 cm $H_2O$, for example) to avoid over-distension of the lung. The target patient compliance range for the ventilator of the present invention is 20-50 cc/cm $H_2O$. In addition, as the patient improves, and gas exchange improves, less minute ventilation will be required to excrete carbon dioxide, so that the respiratory rate can also be reduced (in the range of 12-15 BPM, for example).

Further, while the patient improves, the patient's oxygen requirements will also decrease, enabling a reduction in PEEP (to as low as 5 cm $H_2O$, for example), and a reduction in $F_iO_2$ (to 40% of its original level, for example). The ability to measure and titrate these variables improves the efficacy and safety of the mechanical rapid response ventilator of the present invention.

Thus, in a second embodiment of the ventilator of the present invention, the operator is able to manipulate the target airway pressure (PIP), PEEP, the level of oxygenation, and the respiration rate. Thus, in a second embodiment, the ventilator of the present invention can more effectively be used in a broader cross-section of patients because it comprises additional controls.

Reference will now be made to a specific embodiment of the rapid response ventilator of the present invention having variable controls. It should be noted herein that while optimal ranges and values are provided, one of ordinary skill in the art should understand that each patient is different and that the mechanical ventilator of the present invention may be operated at levels suitable for a broad variety of patients.

FIG. 5 is a schematic diagram of a second embodiment of the ventilator of the present invention. Referring now to FIG. 5, ventilator 500 comprises a compressed gas interface 505, which further comprises a compressed gas reservoir 599, which in use, is connected to a pressurized gas source (not shown) via interface 505. In one embodiment, the pressurized gas is oxygen. In another embodiment, the pressurized gas is medical compressed air. In one embodiment, compressed gas interface 505 is an inlet port.

In operation, a compressed gas is supplied to ventilator 500 from a source, such as a tank, preferably at a pressure greater than 5 PSI. In one embodiment, the compressed gas is oxygen. A gas regulator (not shown) regulates the delivery of compressed gas at a suitable pressure for use within the ventilator unit 500. In one embodiment, a suitable pressure for the compressed gas supply is in the range of 5 PSI to 60 PSI. In one embodiment, a suitable pressure for the compressed gas supply is 50 PSI. In another embodiment, a suitable pressure for the compressed gas supply is 30 PSI.

Inhalation is enabled by delivering regulated oxygen through gas control valve 510 and through inhalation conduit 515 and to flow control valve 525, thus increasing the pressure in inhalation conduit 515. The resultant pressure in inhalation conduit 515, caused by flow control valve 525, is passed, via non return valve 590 to branch conduit 545, which subsequently actuates the expiratory valve 540. Once actuated, expiratory valve 540 seals exhaust port 535, enabling oxygen delivery to the patient and resulting in a pressure increase.

In one embodiment, the oxygenation level can be varied to provide a mixture of oxygen and air. In one embodiment, the control is variable, with three $O_2$/air ratio settings: 100%, 75%, and 50%. In another embodiment, the control is variable to provide two O$_2$/air ratio settings: 100% and 60%. This is achieved by an air entrainment arrangement area 591, which uses a venturi effect to deliver 60% oxygen. Atmospheric air enters the mechanism via a non-return valve 592. The non-return valve 591 can be closed via cover 593, allowing 100% delivery of oxygen.

Ventilator 500 further comprises gas control valve 510. Gas control valve 510 is connected to compressed gas reservoir 599 on one end. At the other end, gas control valve 510 is connected to inhalation conduit 515. Inhalation conduit 515 is operationally connected to patient interface 520 via flow control valve 525.

In one embodiment, flow control valve 525 is a knob, capable of being manipulated to control breath rate. In another embodiment, flow control valve 525 is a fixed jet, delivering a breathing rate proportional to patient size.

In one embodiment, an optimal respiration rate is in the range of 15-35 BPM. In order to achieve a variable respiration rate, it should be noted that in one embodiment, the inspiratory time is fixed while the expiratory time is variable. For example, to achieve 20-35 BPM, the inspiratory time is fixed at 1 second while the expiratory time ranges from 0.8 to 2 seconds. In another example, to achieve 15-35 BPM, the inspiratory time is set to 1 second with a variable expiratory time range of 0.8 to 3 seconds±0.1 second.

In one embodiment, the respiration rate control is an un-calibrated variable control. In another embodiment, the respiration rate control is an un-calibrated, detented control. In one embodiment, the control is labeled at its settable limits, such as low and high or such as low, medium, and high.

In one embodiment, patient interface 520 further comprises a patient interface 520a for accepting air from the patient and patient interface 520b for delivering oxygen to the patient.

In one embodiment, patient interfaces 520a and 520b is connected to a breathing mask. In another embodiment, patient interfaces 520a and 520b are connected to an endotracheal tube. In yet another embodiment, patient interfaces 520a and 520b are connected to a laryngeal mask airway (LMA) device. Laryngeal mask airway devices are well-known to those of ordinary skill in the art and are used in anesthesia and emergency medicine for airway management. More specifically, it is a tube with an inflatable cuff that is inserted into the pharynx. It causes less pain and coughing than an endotracheal tube, and is easier to insert. It should be noted, however, that the laryngeal airway mask is not recommended for anyone at risk for lung aspiration.

Inhalation conduit 515, which is proximate to interface 520b, extends from patient interface 520b into an exhalation interface, which comprises exhaust port 535. Exhaust port 535 is controlled by expiratory valve 540, in communication with branch conduit 545 and connected to inhalation conduit 515, which is proximate to gas control valve 510.

In one embodiment, a PEEP control mechanism is connected to expiratory valve 540. The PEEP control is then set, using PEEP valve 585, as indicated by the patient's oxygenation indications.

In one embodiment, PEEP is a variable control. In one embodiment, PEEP is variable from 5 cm H$_2$O to 20 cm H$_2$O. In another embodiment, PEEP is variable from 10 cm H$_2$O to 20 cm H$_2$O. In one embodiment, PEEP is a continuously variable control. In another embodiment, PEEP is controlled in increments of 5 cm H$_2$O. In one embodiment, at extubation, PEEP should be less than 10 cm H$_2$O and more specifically, from 5-8 cm H$_2$O.

In one embodiment, the ventilator of the present invention also comprises a pressure detector 514. In one embodiment, pressure detector 514 is employed as an interface to the alarm system described in FIG. 4. In one embodiment, pressure detector 514 is an electronic diaphragm actuator that translates activity within the ventilator into a signal that can be used to alarm the operator upon pre-determined events, as described in further detail below.

Referring back to FIG. 5, in one embodiment, the ventilator of the present invention operates in Pressure Control Mode, thus the inspiratory time is controlled by pressure. In one embodiment of the present invention, airway pressure control 581, located proximate to patient interface 520b, is employed to set the target patient pressure in the control system. In one embodiment, an integrated, pneumatic, inspiratory airway pressure gauge or monitor 549 is provided in the ventilator 500 of the present invention. The gauge is employed to display the instantaneous airway pressure value ranging from 0 to 50 cm H$_2$O.

Gas flows along conduit 555 and inflates diaphragm actuator 550. When actuator 550 is inflated, valve 551 is opened via push rod 552. This allows gas from conduit 545 to inflate diaphragm 553, which results in action by pushrod 556 and snap action dome spring 558, which results in the actuation of gas control valve 510, in response to the movement of diaphragm 550. Gas control valve 510 is closed to shut off gas supply. Leak jet 560 serves to allow diaphragm 550 to reset after actuation.

In some cases, as described above, a patient may exhibit a greater compliance (meaning that the patient is improving), and thus, the current setting of the pressure control of the inspiratory time could lead to over-inflation of the lungs. Therefore, the ventilator system of the present invention further comprises a timeout mechanism that limits the inspiratory flow. In one embodiment, the timeout mechanism limits inspiratory flow to approximately 0.9 seconds.

In one embodiment, the inspiratory flow can be set at a value in a range from a minimum value of 60 L/min to a maximum value of 100 L/min.

Referring back to FIG. 5, gas from conduit 545 flows through flow restrictor 562 and inflates diaphragm 553 via conduit 564, causing gas flow valve 510 to close, shutting off the gas flow.

After the gas flow has stopped via the closing of gas flow valve 510, leak jet 575 allows pressure in conduit 545 to dissipate, allowing expiratory valve 540 to open after a pre-set time interval. Conduit 564 is closed by valve 566, which is held closed by pressure in conduit 568.

Gas in conduit 568 is allowed to dissipate through valve 582. In addition, after the inspiratory flow is stopped, after a time interval that is set by pressure in valve 582, valve 566 is allowed to open, which vents conduit 564 and releases the pressure holding inspiratory valve 510 closed and the cycle restarts.

In one embodiment, the pressure is suitable for most patients without causing any patient injury. In one embodiment, the ventilation pressure is variable and set by the operator. In one embodiment, the ventilator 500 operates in a range of 10 cm H$_2$O to 70 cm H$_2$O. In another embodiment, ventilator 500 operates in a range of 15 cm H$_2$O to 40 cm H$_2$O. In one embodiment, the ventilator 500 operates at a maximum of 35 cm H$_2$O. In another embodiment, the ventilator 500 can provide pressure-controlled ventilation at a pre-set pressure of 25 cm H$_2$O. Pressure relief valve 502 is located in the circuit to the patient that is set to ensure that over-pressure is not delivered to the patient.

In one embodiment, the target airway pressure, or PIP, is a variable control and is labeled at its settable limits ranging from a minimum of 15 cm $H_2O$ and a maximum of 40 cm $H_2O$. In one embodiment, the PIP control further comprises a safety interlock, which is activated or interlocked at pressures above 35 cm $H_2O$.

In one embodiment, the ventilator of the present invention is manufactured using pre-fabricated tooling. Preferably, the tooling is pre-fabricated and stored at predetermined, strategic manufacturing sites. This embodiment is particularly useful when employed in global pandemic situations, where a high volume of units would need to be manufactured quickly and effectively. Thus, in one embodiment, the ventilator of the present invention can be manufactured in large quantities from a set of tools that can be used in response to global pandemic situations. In one embodiment, the tool-set is fabricated from high grade steel.

In one embodiment, the ventilator of the present invention is manufactured using tooling fabricated from a material of lower durability than steel at the onset of an epidemic. In one embodiment, the material of lower durability is aluminium. Preferably, the materials are readily accessible to produce a more limited number of units for more localized outbreaks of disease. The tooling can be manufactured fairly rapidly.

In one embodiment, the ventilator of the present invention is manufactured using parts that are fabricated in an automated system directly from design documentation. Thus, in this embodiment, no tooling is actually created. This embodiment is particularly useful for supporting remote areas where the ultimate goal is to transport patients to larger centers but temporary respiratory support is nevertheless required. Advantageously, the manufacturing method of the present invention allows for the ventilators to be produced on demand without the time it takes to manufacture the tooling.

In each of the manufacturing embodiments described above, assembly is simple and does not require highly specialized skills or training.

The ventilator can be used effectively and safely by minimally trained caregivers in a wide variety of care settings to provide respiratory relief to patients.

In addition, the ventilator of the present invention is effective in keeping alive a majority of patients with severe respiratory infections that do not have other serious complications, or those that typically would be placed on traditional ventilators.

In one embodiment, the ventilator of the present invention is tested to ensure that operational performance is within proper predetermined ranges or margins. In another embodiment, the ventilator of the present invention is capable of providing at least one alert to an operator when life expectancy or operational performance ranges or margins of the device are exceeded.

In one embodiment of the rapid response ventilator of the present invention, the ventilator is capable of operating independent of electrical supplies.

In another embodiment, the rapid response ventilator is powered by oxygen at a regulated pressure.

In another embodiment the rapid response ventilator of the present invention is battery-operated.

In one embodiment, the rapid response ventilator of the present invention further comprises an alarm system.

In one embodiment, the rapid response ventilator of the present invention has an audio and/or visual alarm that alerts upon battery failure, or when the battery voltage falls below an acceptable pre-determined level. Thus, in one embodiment, the electronics of the alarm system are powered by a battery, such as a manganese-alkaline battery, a mercury type battery or any other suitable battery known to persons of ordinary skill in the art. When the battery voltage reaches a pre-determined, factory set voltage level a visual alarm is activated, such as the L.E.D. will start flashing in RED. Optionally, the alarm will also emit an audible alarm, such as a clicking sound. This is indicative that the battery needs to be changed. In one embodiment, the low battery voltage condition is set to sense when the battery voltage is less then 2.5 volts.

The alarm system is also capable of sensing the internal activity of the ventilator and upon sensing an alarm condition will provide a visual and/or audible output. In one embodiment, an alarm condition is low supply gas pressure. In another embodiment, an alarm condition is disconnection from the patient. In yet another embodiment, an alarm condition is failure to ventilate.

Thus, the alarm system is used to provide an audible and/or visual apnea alarm. In one embodiment, the alarm system causes an L.E.D. to emit a short flash, preferably green, with each breath to confirm that the ventilator system of the present invention is fitted and working properly. If no breaths are detected within a pre-determined time period, an audible and pulsating beep is emitted in conjunction with a flashing L.E.D., preferably RED, to identify that the alarm system of the ventilator of the present invention is in an alarm state. In one embodiment, the pre-determined time period between breath detection is factory pre-set and in the range of 15 to 20 seconds.

In one embodiment, as described above with respect to FIG. 5 and referring back to FIG. 5, the alarm system is operably connected to the ventilator of the present invention via an electronic diaphragm actuator 514. Specifically, the diaphragm actuator 514 is operably connected to a PCB (not shown), via a plunger on the electronics diaphragm actuator, which moves once per breath under the pneumatic action of the ventilator, and thus initiates sensing activity of the alarm system. The PCB also provides support for the power/battery components via connection to the battery terminals, as shown in FIG. 4. In addition, the audible alarm and LEDs are aligned with the ventilator system of the present invention to allow the sound and light to pass through such that they can operate as visible and audible alerts to the operator. In one embodiment, a change in pressure is detected by the diaphragm actuator which translates activity within the ventilator, into a signal that can be used by the PCB to alarm a pre-determined event, such as displacement of the diaphragm under pressure due to an increase in pressure.

In one embodiment, upon inhalation of the first breath by the patient, the battery supplies power to the alarm system so that it is deployed and thus, the alarm is ready to detect an alarm condition automatically on the occurrence of the first breath, minimizing the risk of an operator forgetting to deploy the alarm. Subsequent breaths alternate between inspiration during which air is supplied by the ventilator to the patient's lungs and expiration during which air passes out of the exhalation valve.

In another embodiment, the ventilator of the present invention is capable of responding to patient need. More specifically, in one embodiment, if a patient begins to resume breathing spontaneously, the ventilator of the present invention is capable of entering a passive mode. In another embodiment, if a patient fails to maintain spontaneous unassisted breath, the ventilator begins to operate and assist with oxygen delivery to the patient.

In one embodiment, the ventilator of the present invention additionally employs a mechanical trigger to indicate that a patient is breathing spontaneously and to initiate action, such as patient ventilation. Prior art triggers either use electricity powered electronics/software to aid in the detection of a breath or simply allow the user to spontaneously breathe atmospheric pressure air rather than actually triggering a ventilator to provide an assisted breath and in some cases, wean the patient off of ventilation. The mechanical trigger of the ventilator of the present invention requires a minimal number of source parts and is thus easy to manufacture. Thus, in one embodiment, spontaneous breathing triggers SIPV (Synchronized Intermittent Pressure Ventilation). This allows the ventilator to be used with patients that are not sedated and synchronizes to the patient's own attempts to breath giving pressure support to assist the patients breathing effort.

Figure 6A:
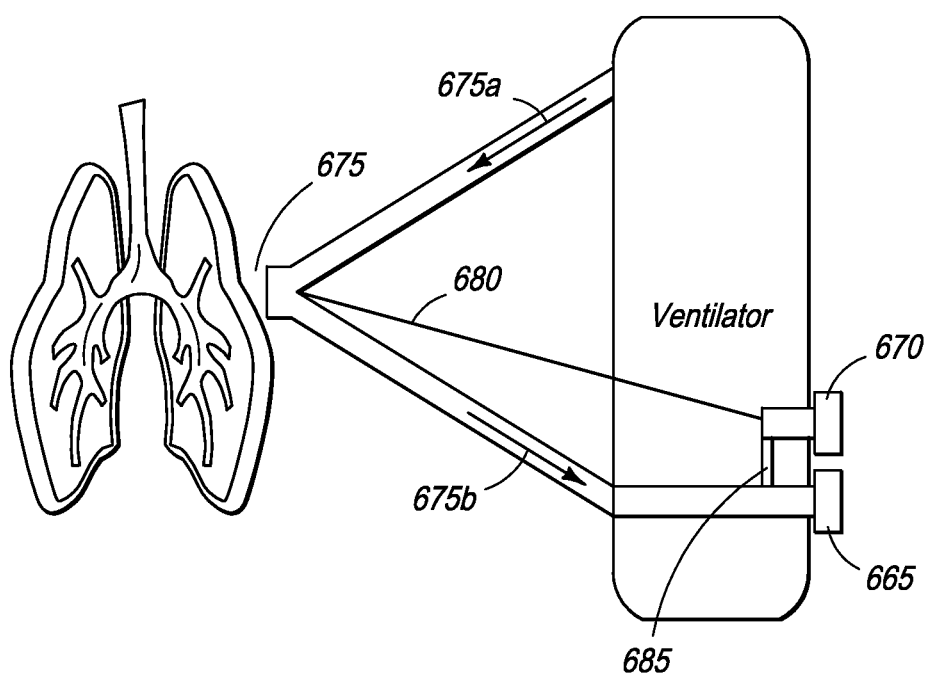
FIG. 6a is a schematic diagram of the ventilator of the present invention further equipped with a mechanical trigger.

FIG. 6a is a schematic diagram of the ventilator of the present invention further equipped with a mechanical trigger. As shown in FIG. 6a, ventilator 660, in one embodiment, further includes PEEP valve 665 and mechanical trigger 670.

In one embodiment, the mechanical trigger employed in the present invention is a PEEP-referenced spontaneous trigger. PEEP (Positive End-Expiratory Pressure) refers to the residual positive pressure that remains in the airway at the end of the expiratory cycle. The PEEP control is set as indicated by the patient's oxygenation levels and is employed to prevent the lung from fully collapsing after each breath, thus improving gas exchange in the lung.

The ventilator 660 further includes patient connection area 675 which leads to a mouthpiece (not shown), which further comprises an inlet 675a (to patient) and an exhaust 675b (from patient). Exhaust 675b is connected to the patient at its distal end and to the PEEP valve 665 at its proximal end, wherein the proximal end is the end attached to ventilator 660. In addition, in one embodiment, the ventilator 660 includes a thin bore pipe 680 that leads to the mouthpiece (not shown) near patient connection area 675. Further, a direct link to airway 685 is provided and provides a connection between the mechanical trigger 670 and exhaust 675b.

Figure 6B:
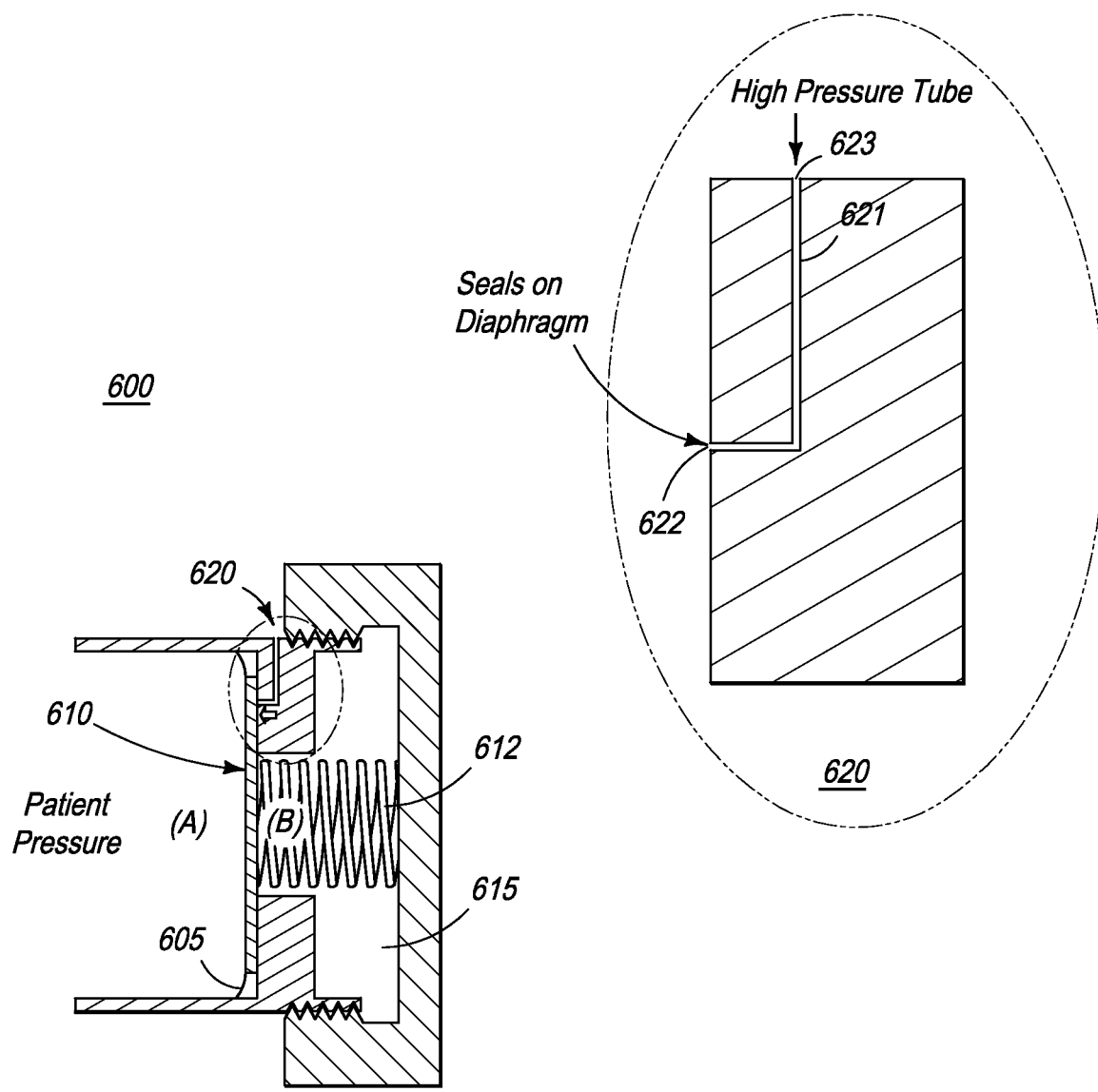
FIG. 6b is a schematic illustration of a first embodiment of a mechanical trigger used in the ventilator of the present invention.

FIG. 6b is a schematic illustration of a first embodiment of a mechanical trigger used in the ventilator of the present invention. Mechanical trigger 600 comprises diaphragm 605, which further comprises a first side 610 and a second side 615. Mechanical trigger 600 also comprises spring 612, which, in one embodiment, is positioned abutting second side of diaphragm 615. Airway pressure emanating from a patient (not shown) acts on first side 610 while atmospheric air pressure and spring 612 act on second side 615. A high pressure pilot valve 620 is created by positioning a small diameter tube 621 with an end 622 facing second side 615 of diaphragm 605 and an end 623 connected to a high pressure air supply. In one embodiment, the ends 622, 623 of tube 621 form an opening for receiving or expelling air. Physical displacement of the diaphragm 605 is used as a trigger for the ventilator by either a) making a mechanical connection to the diaphragm or b) releasing a high pressure pilot valve.

Figure 6C:
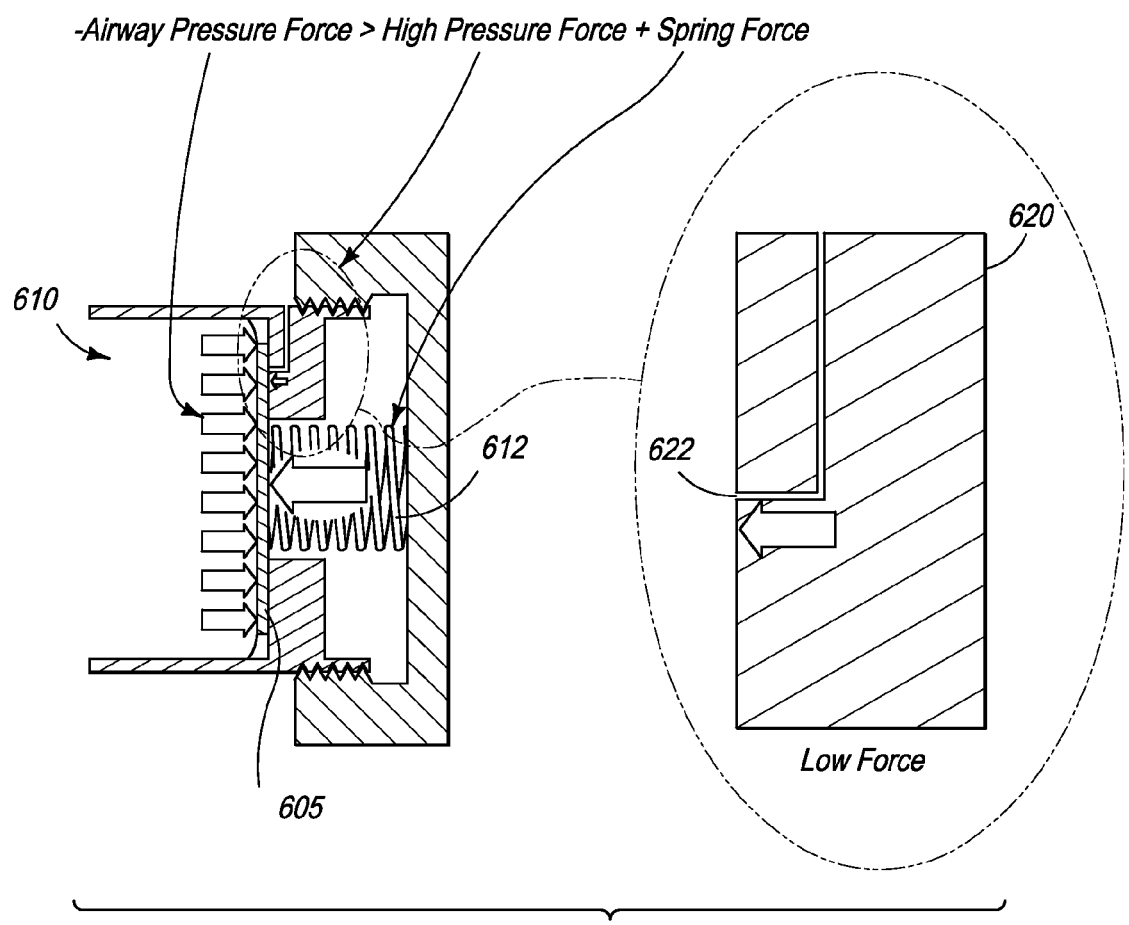
FIG. 6c depicts the mechanical trigger shown in FIG. 6b during normal operation of the ventilator.

FIG. 6c depicts the mechanical trigger shown in FIG. 6b during normal operation of the ventilator. As shown in FIG. 6c, during normal operation the airway pressure force from a patient, impinging on first side 610, is greater than the combined force, of both spring 612 and the high pressure air supply emanating from valve 620, impinging on second side 615. As a result, the diaphragm 605 is firmly pressed against the open end 622 of valve 620, thereby sealing open end 622.

Figure 6D:
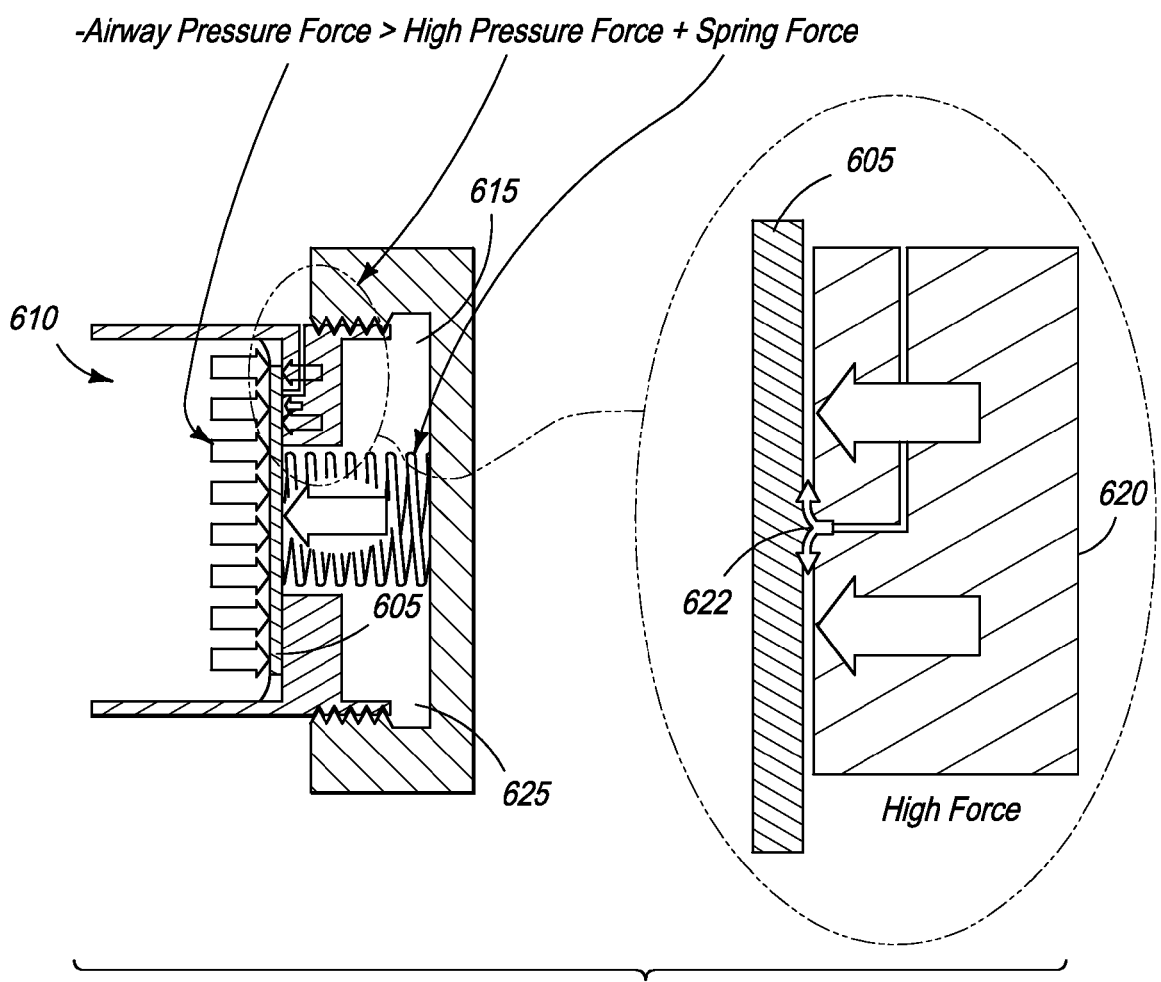
FIG. 6d depicts the mechanical trigger shown in FIG. 6b, while the trigger is activated.

FIG. 6d depicts the mechanical trigger of FIG. 6b, in a triggered state. Thus, as shown in FIG. 6d, the movement of the diaphragm can be used to provide a "trigger" for the ventilator of the present invention. As the airway pressure emanating from the patient drops (during an inhale, for example), the balance of forces across the diaphragm 605 change, thus causing the diaphragm 605 to move towards the patient airway pressure side 610 and away from end 622 of the valve 620. The movement of diaphragm 605 causes high pressure air to be released into chamber 625 at second side 615 of the diaphragm 605.

Thus, in one embodiment, by restricting the flow of air out of the side of chamber 625, the high pressure can be used to provide a trigger by allowing a pressure build-up. Allowing the pressure to build up at side 615 of diaphragm 605 and in chamber 625 provides a significant mechanical force that is mechanically extracted to provide a trigger.

Figure 6E:
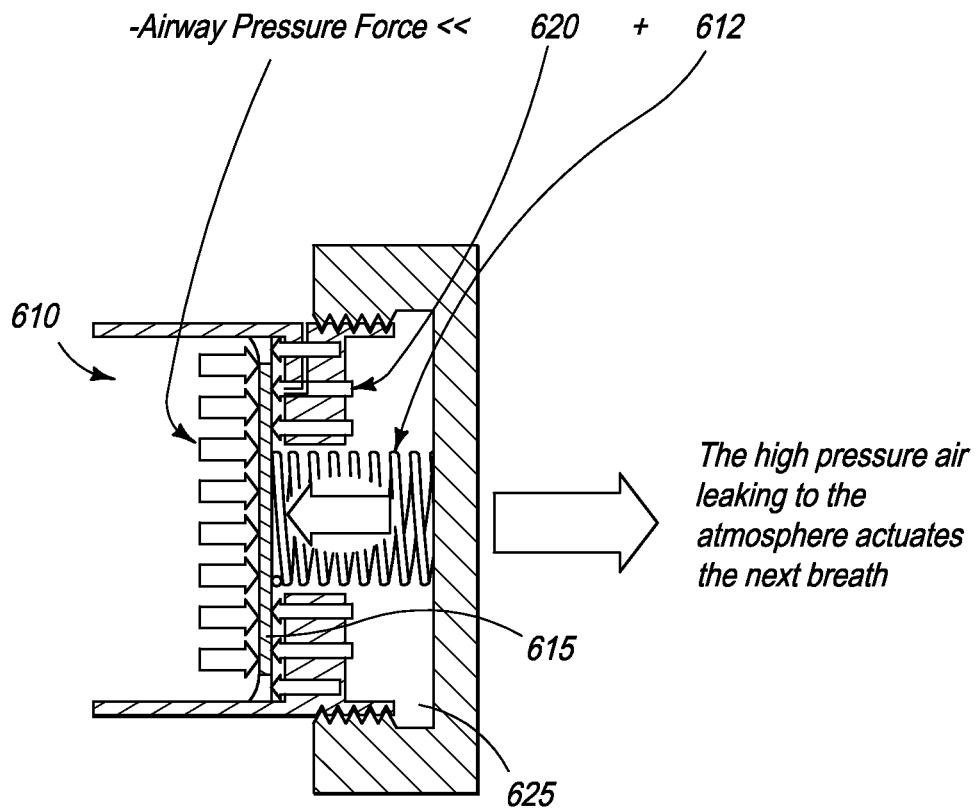
FIG. 6e depicts the mechanical trigger shown in FIG. 6b, after the trigger.
Figure 6F:
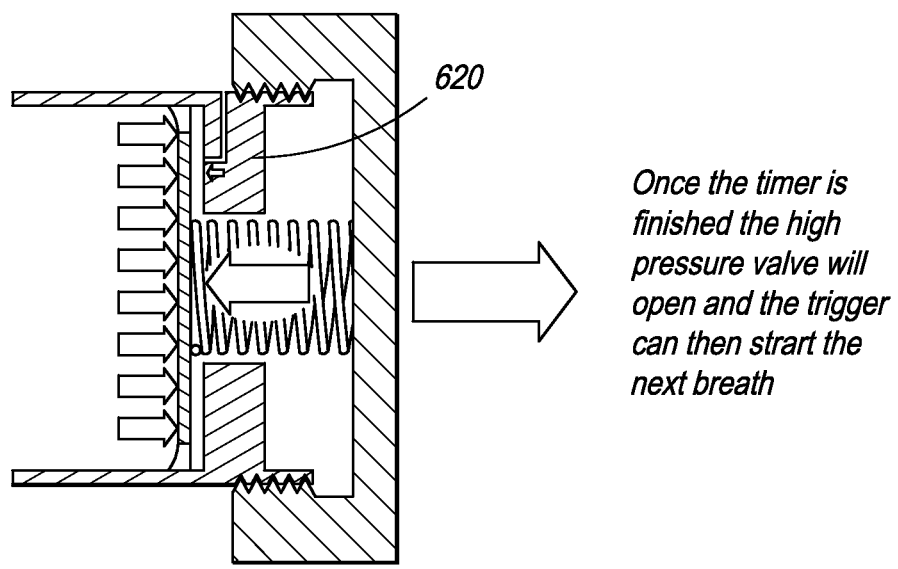
FIG. 6f depicts the mechanical trigger shown in FIG. 6b, further comprising a trigger disabling timer.

6e depicts the mechanical trigger shown in FIG. 6b, after the trigger is in an active state. As shown in FIG. 6e, after trigger, the airway pressure force from a patient, impinging on first side 610, is much less than the combined force, of both spring 612 and the high pressure air supply emanating from valve 620, impinging on second side 615. The high pressure air leaking to the atmosphere actuates the next breath, as the ventilator is in a triggered state. Thus, in another embodiment, the released high pressure can be used to provide a trigger by detecting the pressure drop in the high pressure tube of valve 620 by allowing the chamber 625 to be open to atmospheric pressure.

6f depicts the mechanical trigger shown in FIG. 6b, further comprising a trigger disabling timer. In one embodiment, a timer is employed to disable the trigger in order to prevent triggering during the first 1.5 seconds after inhalation. The trigger is disabled by preventing the high pressure air flowing to the servo even if the trigger is open. Once the timer is finished, the high pressure valve will open, and the trigger can then start the next breath.

Figure 6G:
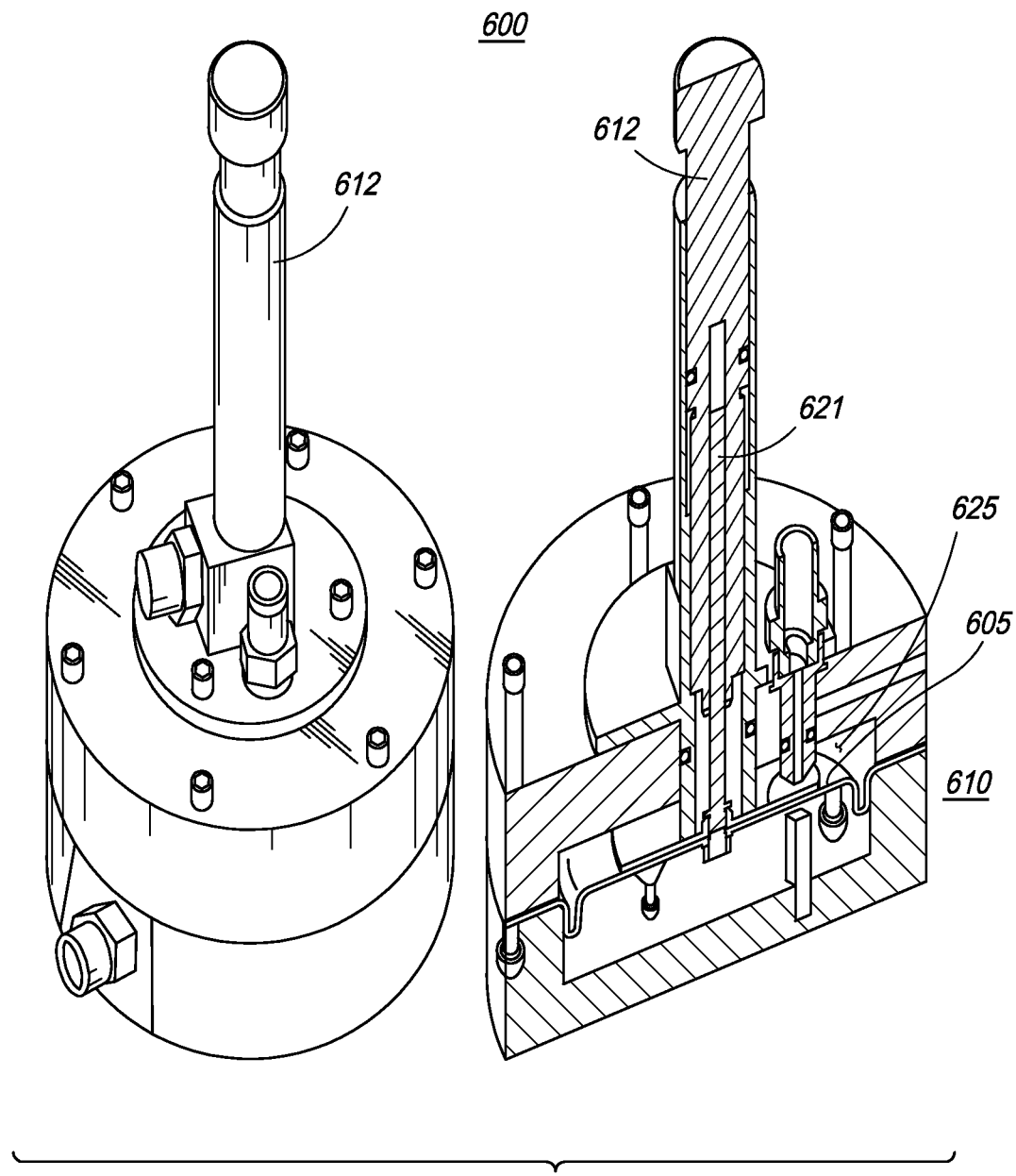
FIG. 6g is a three-dimensional illustration of the mechanical trigger shown in FIG. 6b.

FIG. 6g is a three-dimensional illustration of a mechanical trigger 600. In one embodiment, the spring 612 and thus, adjustment of the spring pressure is mechanically linked to a PEEP valve. Thus, the trigger can maintain a trigger relative to the PEEP pressure, hence requiring no additional settings to the normal setting of PEEP pressure. FIG. 6g also illustrates first side or chamber 610, which is connected to a patient, diaphragm 625, chamber 625, and high pressure tube 621, as positioned in at least a portion of the ventilator assembly.

Figure 6H:
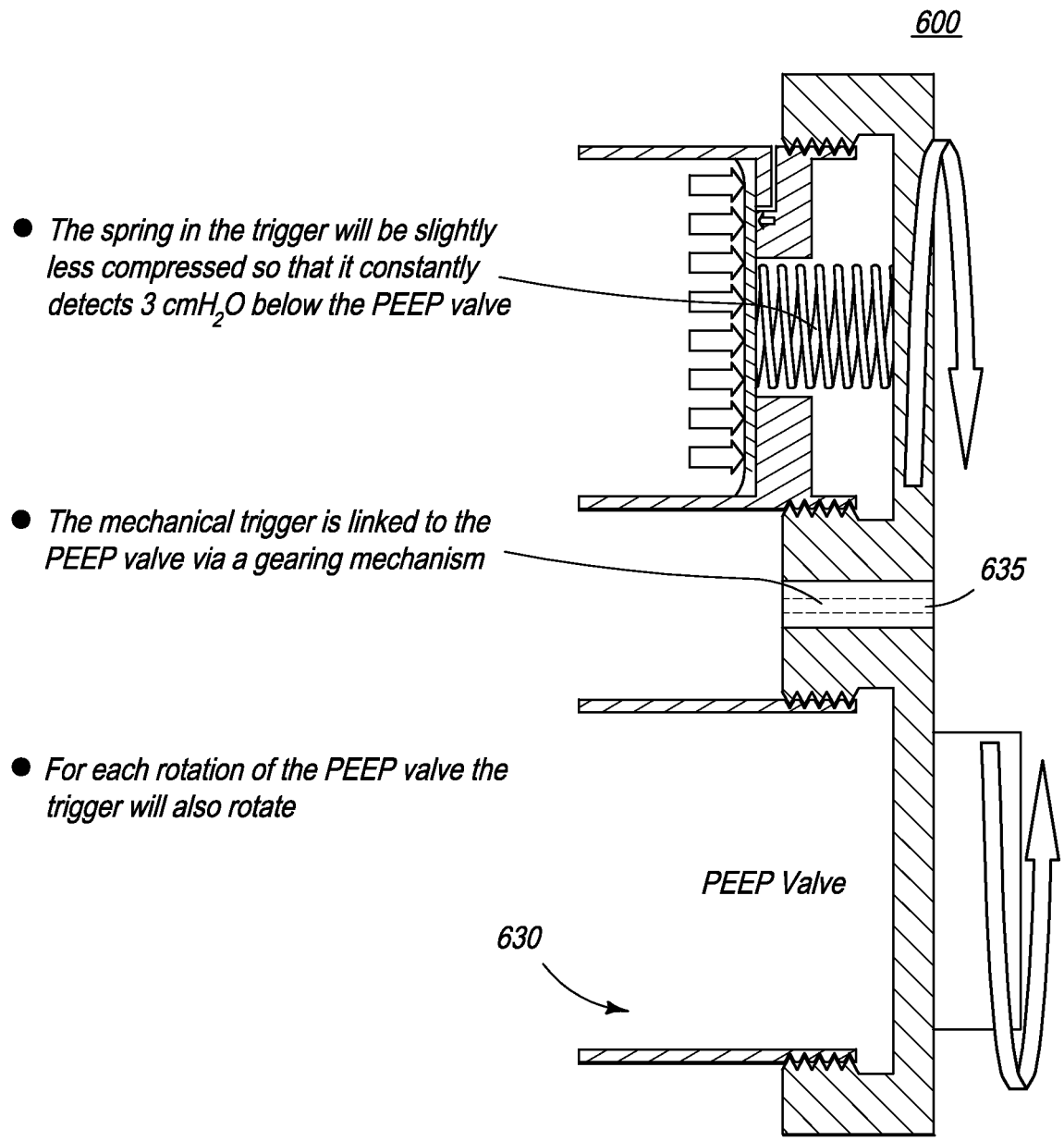
FIG. 6h shows a gear mechanism which, in one embodiment, connects the mechanical trigger to the PEEP valve.

FIG. 6h shows a gear mechanism which, in one embodiment, connects the mechanical trigger shown in FIG. 6g to a PEEP valve. As shown in FIG. 6h, spring 612, and the adjustment of pressure of spring 612 is mechanically linked to a PEEP valve 630 via a gearing mechanism 635. For each rotation of PEEP valve 630, mechanical trigger 600 also rotates. This allows mechanical trigger 600 to maintain a trigger threshold relative to PEEP pressure, hence requiring no additional settings to the normal setting of PEEP pressure. Spring 612 can be adjusted to vary the pressure of the trigger point. In one embodiment, spring 612 (shown in FIG. 6g) is slightly less compressed so that it constantly detects 3 cmH$_2$O below PEEP valve 630.

Figure 7:
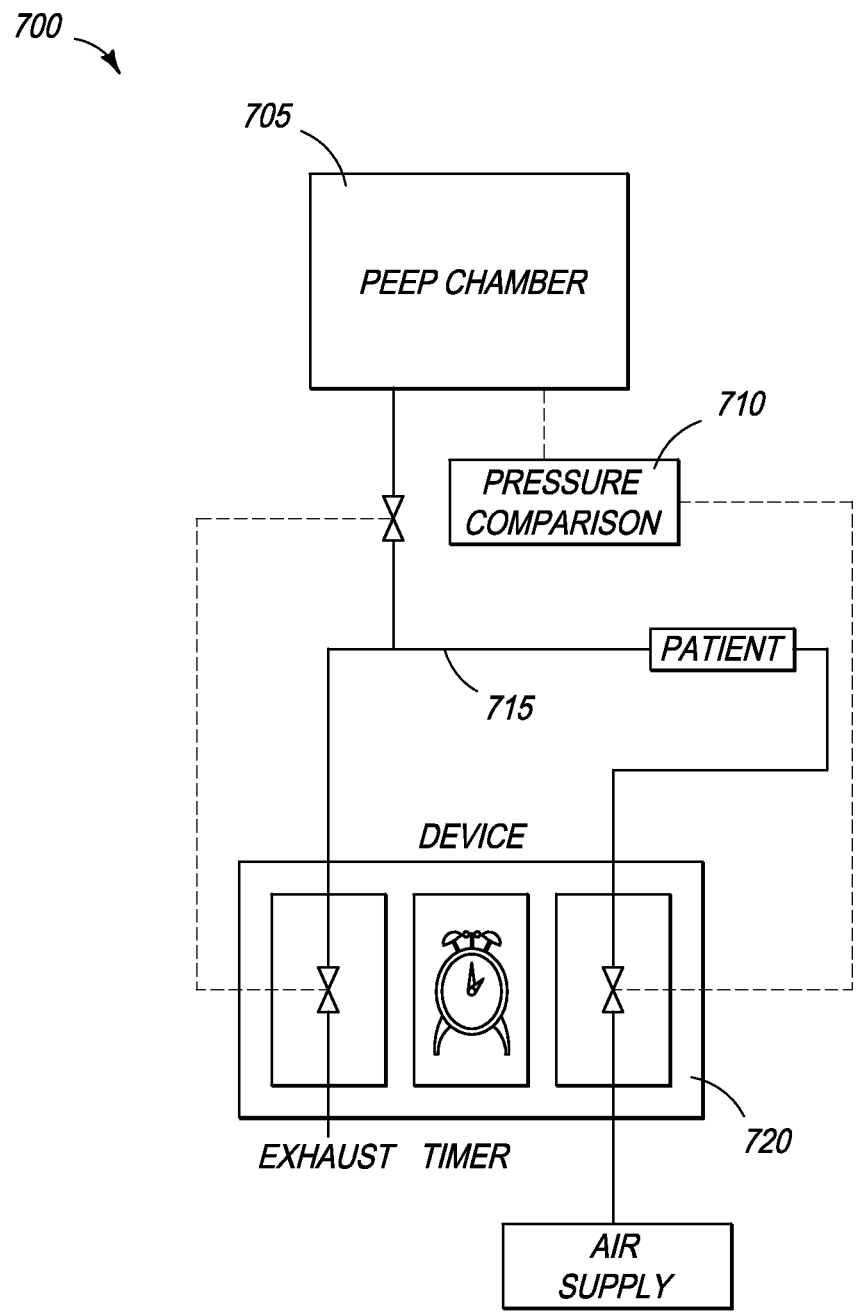
FIG. 7 is a block diagram illustration of a second embodiment of a mechanical trigger used in the ventilator of the present invention.

FIG. 7 is a block diagram illustration of a second embodiment of a mechanical trigger used in the ventilator 720 of the present invention. The mechanical trigger system, as shown in FIG. 7, functions by isolating a chamber of gas at a specific pressure (predetermined PEEP) and comparing this pressure to the airway. When the pressure at the airway is at a set pressure below isolated PEEP gas pressure a mechanical trigger signal is produced.

More specifically, in one embodiment, mechanical system 700 functions by isolating chamber 705, which contains gas at a predetermined Positive End Expiration Pressure (PEEP) and then comparing, at block 710, this predetermined pressure to airway pressure at exhaust 715 of the ventilator 720. It should be noted that the set PEEP pressure in the chamber can be "captured" by using the same PEEP valve that is used to set up the normal ventilation function of the machine, as described in greater detail below.

Figure 8A:
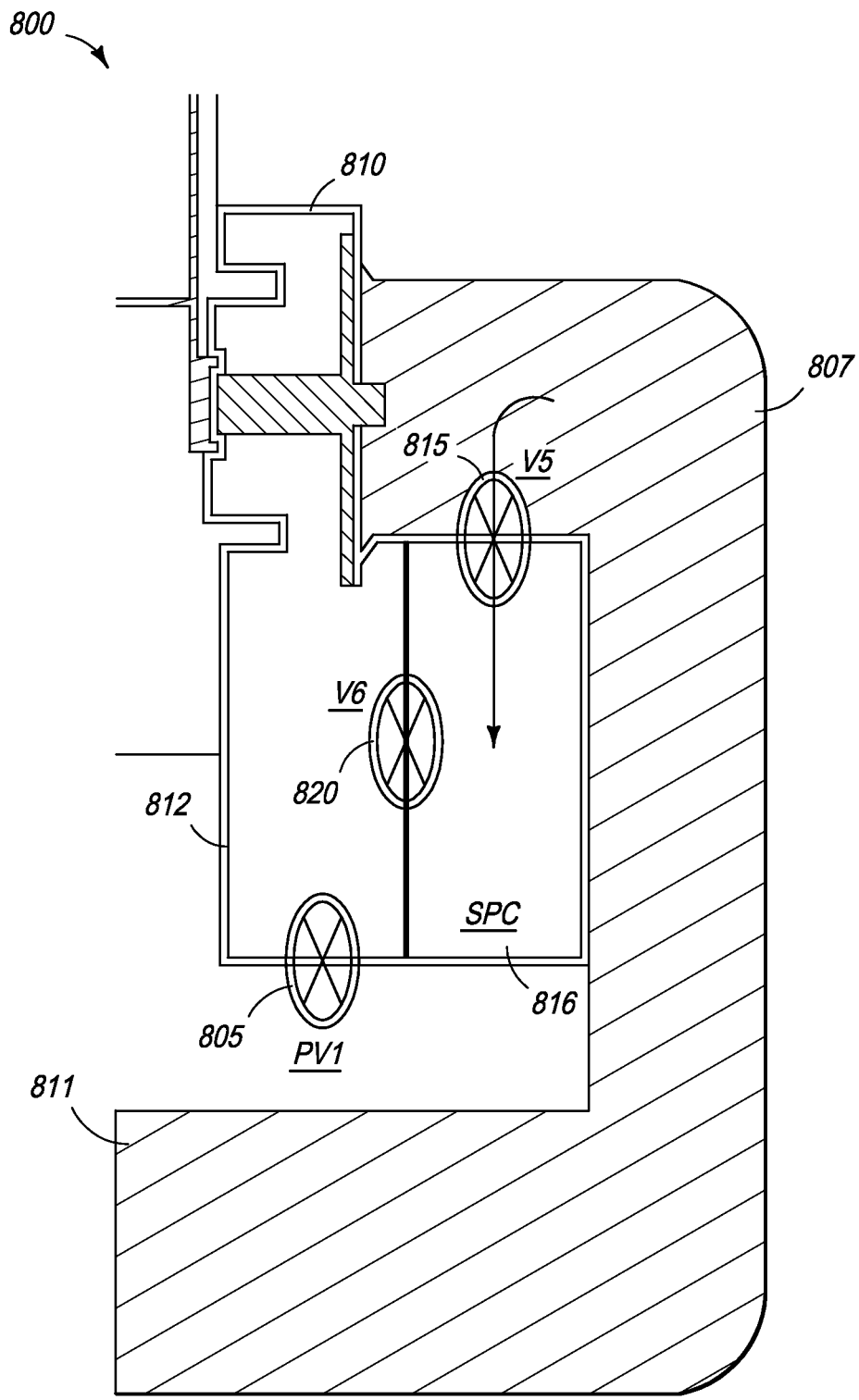
FIG. 8a illustrates one embodiment of a device employed to isolate gas that is at a predetermined PEEP, using the isolating chamber described with respect to FIG. 7.

FIG. 8a illustrates one embodiment of a device employed to isolate gas that is at a predetermined PEEP, using the isolating chamber described with respect to FIG. 7. Device 800 comprises a plurality of valves, including an adjustable pressure relief PEEP valve 805 located in exhaust area 807 of the ventilator system of the present invention. Expiratory valve 810 allows direct communication between the patient airway 811 and exhaust chamber 812. The exhaust chamber 812 is the chamber that all gas exiting the system passes through prior to the PEEP valve 805. Valve 815 allows fluid communication between the patient airway 811 and sample PEEP chamber 816. The PEEP chamber 816 is the chamber used to compare pressure to the airway pressure. Valve 820 allows fluid communication between the sample PEEP chamber 816 and the exhaust chamber 812. The PEEP valve 805 is set to a specific pressure. When pressure in the exhaust chamber 812 is above this predetermined pressure, the PEEP valve 805 is open to allow fluid communication between exhaust chamber 812 and the atmosphere. When pressure in the exhaust chamber 812 is below this predetermined pressure the PEEP valve 805 remains closed. By opening and closing the plurality of valves, as described above, it is possible to trap a volume of air in sample PEEP chamber 816 that is at the same predetermined pressure level that PEEP valve 805 is set to close at.

Figure 8B:
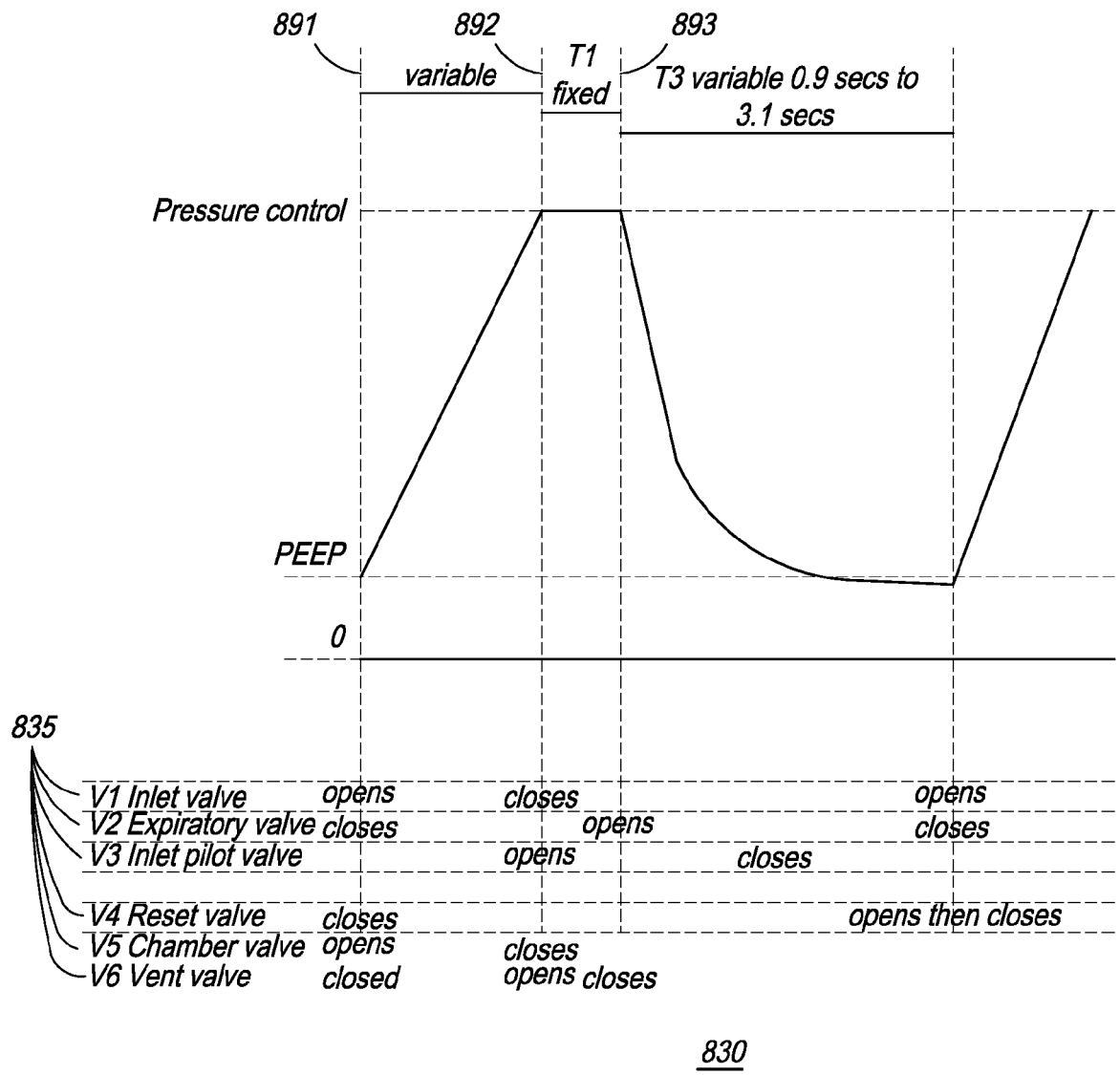

FIG. 8b is a graph depicting a typical ventilation cycle of pressure against time and further depicts operation of the plurality of valves of the device shown in FIG. 8a. In particular, graph 830 shows when each of the plurality of valves 835 opens and closes, in the cycle of pressure versus time, to accurately capture the reference PEEP pressure in sample PEEP chamber 816. Graph 830 shows stage one 891, stage two 892, and stage 3 893, described in further detail below.

Figure 8C:
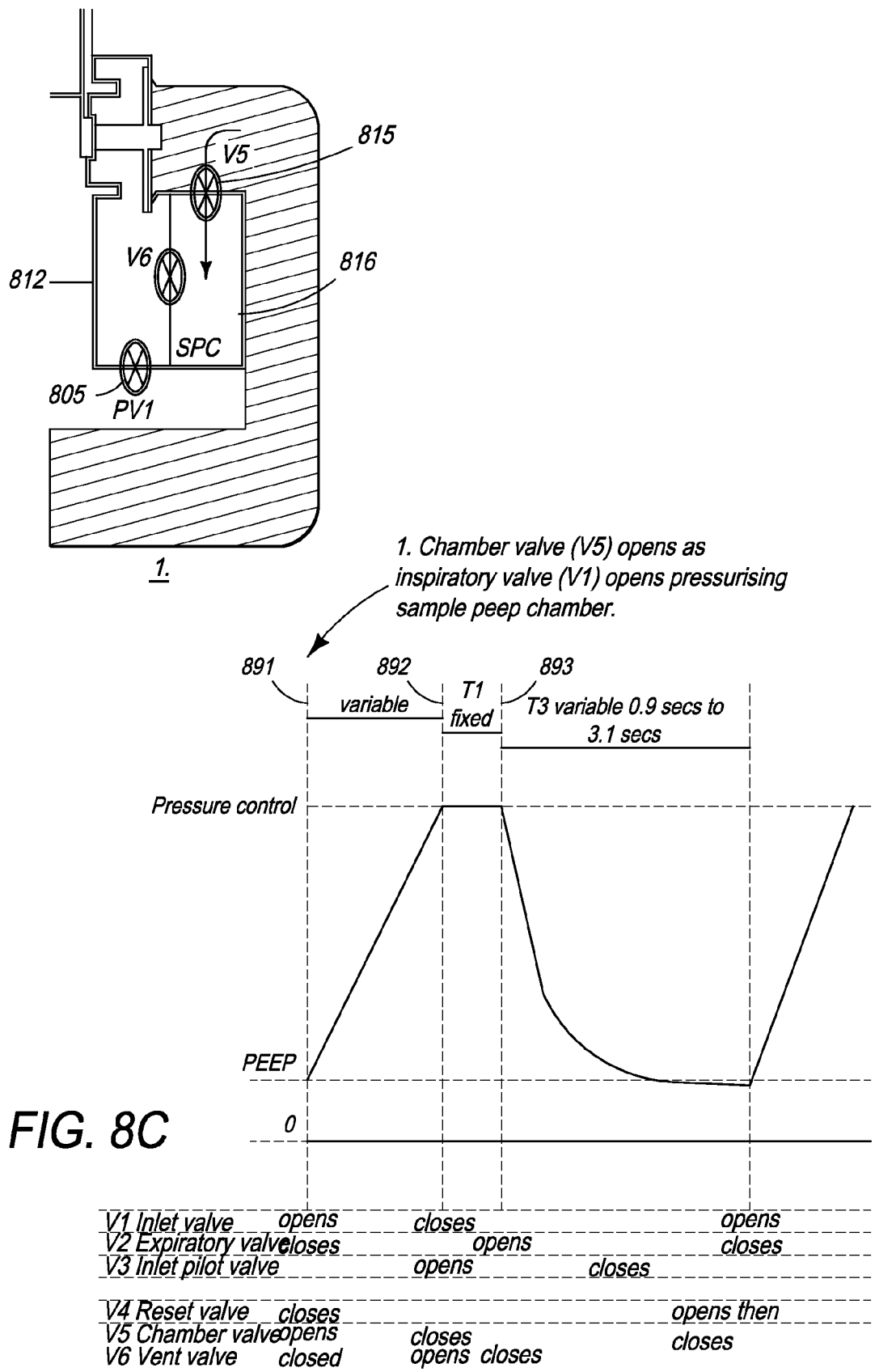

FIG. 8c illustrates a first stage operation of the valves shown in FIG. 8a. In stage one, as shown in FIG. 8c, chamber valve 815, the valve that allows fluid communication between the patient airway and the sample PEEP chamber SPC, opens as PEEP valve 805, the valve that is set to a specific pressure, opens. This results in the pressurization of the sample PEEP chamber 816. Note that when the exhaust chamber 812 is above this set pressure, PEEP valve 805 is open to allow fluid communication between the exhaust chamber 812 and the atmosphere, however when the exhaust chamber 812 is below this set pressure, the PEEP valve 805 is closed.

Figure 8D:
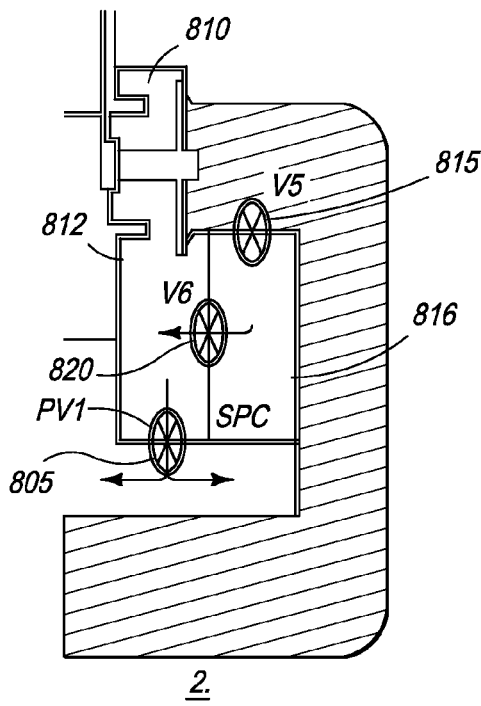
Figure 8D:
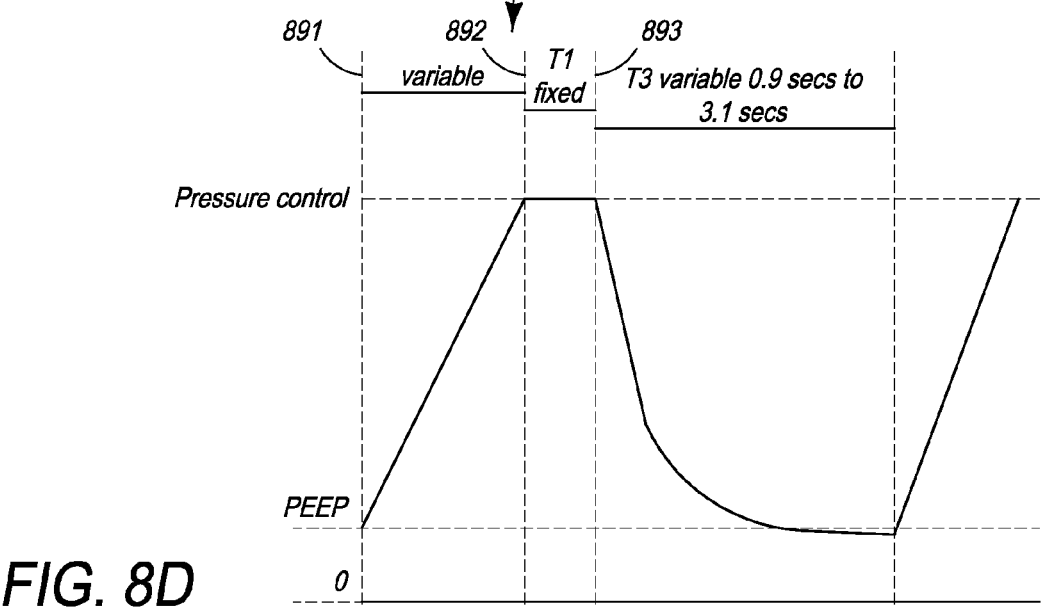

FIG. 8d illustrates a second stage operation of the valves shown in FIG. 8a. In stage two, just before expiratory valve 810 (the valve that allows direct fluid communication between the patient's airway and the exhaust chamber 812) opens, valve 815 (the valve that allows fluid communication between the patient airway and the sample PEEP chamber 816) closes and valve 820 (the valve that allows fluid communication between the sample PEEP chamber 816 and the exhaust chamber 812) opens. This results in the pressure in sample PEEP chamber 816 to decay at predetermined, set PEEP through PEEP valve 805.

Figure 8E:
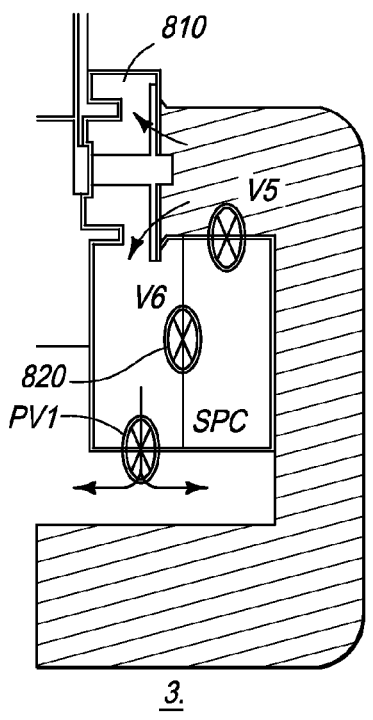
Figure 8E:
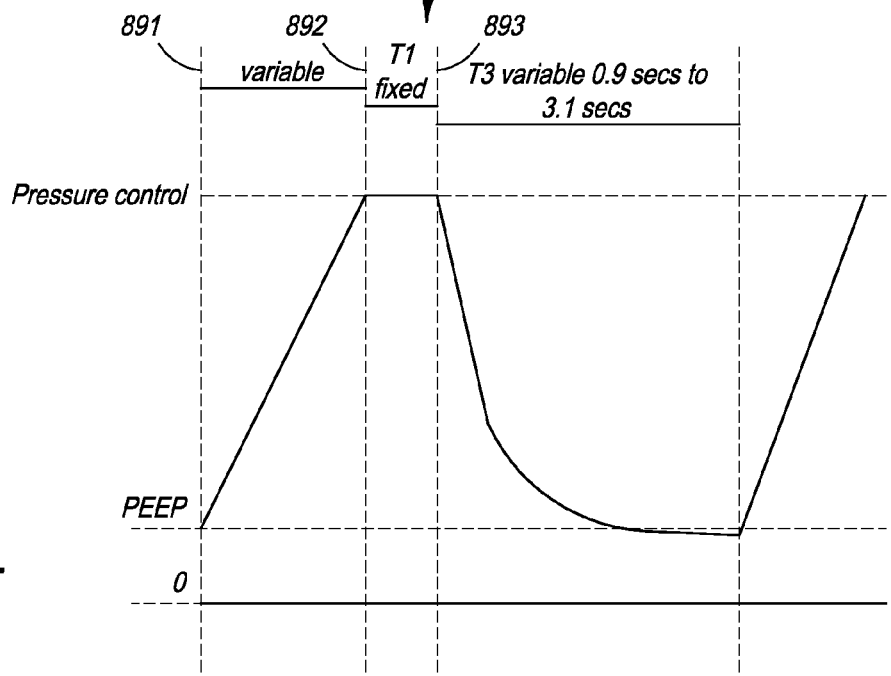

FIG. 8e illustrates a third stage operation of the valves shown in FIG. 8a. In stage three, prior to expiratory valve 810 opening, valve 820 closes. This allows pressure in sample PEEP chamber 816 to be isolated and trapped for comparison with the airway pressure.

Figure 9A:
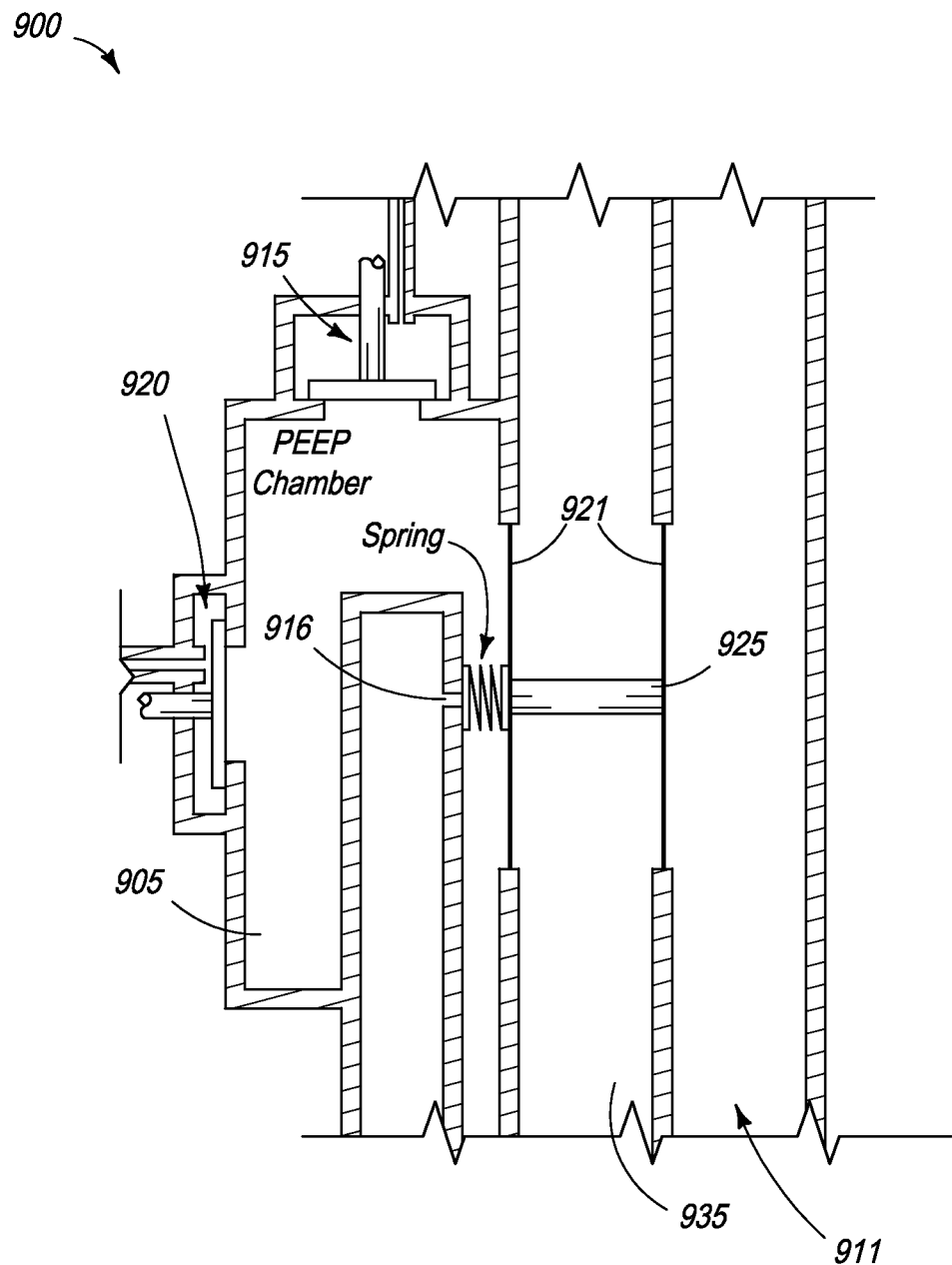
FIG. 9a shows one embodiment of a dual diaphragm device that is used to compare set PEEP with airway pressure.

FIG. 9a shows one embodiment of a dual diaphragm device that is used to compare isolated set PEEP with airway pressure. Device 900 comprises three areas of pressure, including PEEP chamber 905, patient airway 911 (current system pressure) and pilot airway (high pressure) 916. Positioned between the sample PEEP chamber 905 and the patient airway 911 is a dual diaphragm 921 linked by a connecting rod 925. The channel 935 between the two diaphragms 921 containing the rod 925 is at atmospheric pressure. Valve 915 is the valve that allows fluid communication between the patient airway and the sample PEEP chamber. Valve 920 is the valve that allows fluid communication between the sample PEEP chamber and the exhaust chamber.

Figure 9B:
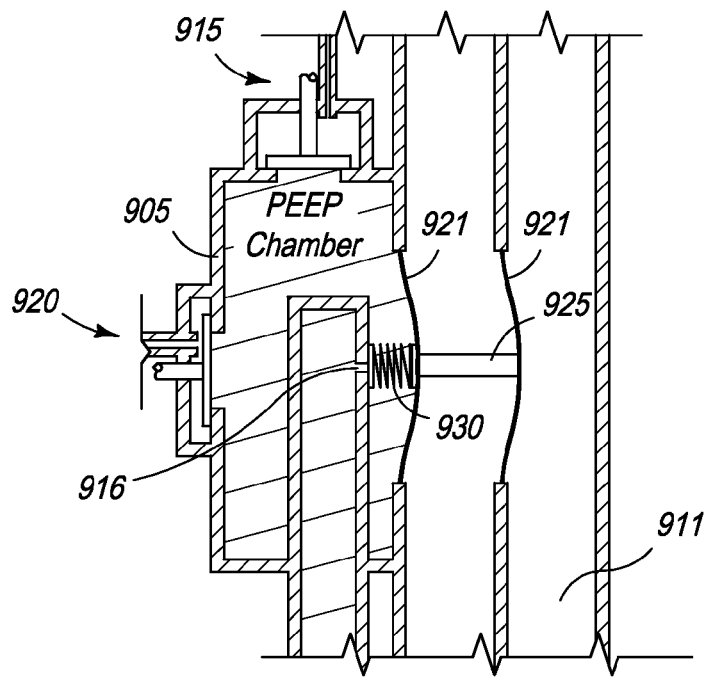
FIG. 9b depicts the dual diaphragm device, shown in FIG. 9a, in triggered state.

FIG. 9b depicts the dual diaphragm device, shown in FIG. 9a, in triggered state. Referring now to FIG. 9b, as pressure in the airway 911 drops, the balance of forces across the dual diaphragms 921 causes the diaphragms 921 to move to the right, aided by spring 930. If the pressure in the airway 911 drops far enough, then diaphragms 921 move far enough to the right to lift spring 930 off pilot airway 916, thus releasing the high pilot airway pressure into the sample PEEP chamber 905. This rise in sample PEEP chamber pressure, owing to the addition of the high pilot airway pressure, forces dual diaphragms 921 further to the right. This additional force is used to drive a mechanical link from connecting rod 925 thereby triggering, for example, the ventilation of the patient.

Figure 9C:
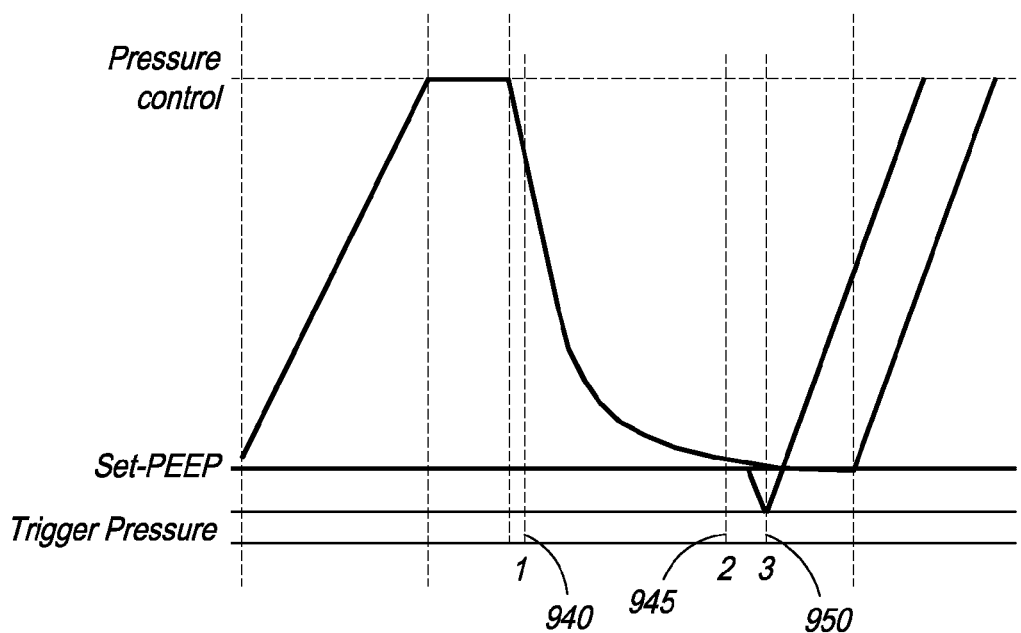
FIG. 9c is a graph depicting the various stages resulting in the movement of the dual diaphragms shown in FIGS. 9a and 9b.

FIG. 9c is a graph depicting the various stages resulting in the movement of the dual diaphragms shown 921 in FIGS. 9a and 9b. At stage one 940, airway pressure is high and PEEP chamber pressure has decayed to set, predetermined PEEP. During stage one 940, there is no movement of diaphragms 921.

At stage two 945, airway pressure is slightly lower than the PEEP chamber pressure causing diaphragms 921 to begin moving. However, at this stage the spring 930 still keeps pilot airway 916 covered.

At stage three 950, airway pressure drops to a pre-set trigger pressure causing the spring 930 to be lifted off the pilot airway 916. This results in high pressure oxygen forcing the diaphragms 921 further into triggered position.

It should be appreciated that the present invention provides for a ventilator with several unique characteristics. First, unlike conventional transport, simple ventilators, the present invention provides for alarms and spontaneous breathing support and can be used to sustain a patient for long periods of time and safely without required monitoring. Second, unlike conventional hospital, complex ventilators, the present invention can operate and provide these advanced features without electricity (other than batteries for the alarm system), complex circuitry or solenoid valves.

In one embodiment, the ventilator of the present invention is robust and can be operated even in situations where a patient is attempting to breathe. Thus, in one embodiment, the ventilator continues to operate normally and reliably in its controlled ventilation mode. The ability to adjust the respiration rate control to match the patient's respiration rate facilitates the robust use of the ventilator.

In one embodiment, the ventilator of present invention is capable of performing over a broad range of lung compliance, rates, and combinations of tidal volume and pressures that include a range of values likely to encompass those most commonly encountered in patients with acute respiratory express during the course of their illness.

In another embodiment, the ventilator of the present invention is capable of providing real time monitoring of $O_2$ saturation, $CO_2$ and respiratory rate. In one embodiment, the rapid response ventilator of the present invention is integrated with discrete modules for monitoring other parameters.

According to one aspect, the present invention is a low cost, quick to manufacture on-demand and easy to use ventilator.

The ease of use of the ventilator is enabled by the fact that its operation is very quickly understood requiring only a few minutes training to grasp the use of the device. This is made possible by having few controls for breathing rate, inspiratory pressure, PEEP and oxygen concentration.

In one embodiment, the present invention is directed toward a disaster response protocol for using the rapid response ventilator of the present invention such that it can be used by any entity, including, but not limited to the government, a third party supplier, a hospital, ambulatory services, family members of the patients, etc.

In one embodiment, all plastic components are pre-made and then assembled in real-time at central logistics sites, military base camps, hospitals and disaster centers. Thus, the present invention is directed towards a protocol for providing a volume of ventilators in response to an epidemic, that includes providing, prior to the epidemic, pre-fabricated tooling for use in manufacturing the ventilators; storing the pre-fabricated tooling in at least one site in proximity to potential epidemic locations; and manufacturing the volume of ventilators at the onset of the epidemic using prefabricated tooling.

In one embodiment, a quick and on-demand anywhere/anytime method of fabricating large volumes of the ventilator of the present invention comprises: obtaining tooling which, in one embodiment, comprises a one piece mold that enables the housing/manifold of the ventilator and the components within the housing/manifold to be made/molded preferably in one/single casting; obtaining simple and readily available electronic components, such as resistors, capacitors, LEDs, small lithium battery, to primarily make and run breath detection and alarm or directly obtaining an electronic PCBA with battery and obtaining requisite clip-on connectors and/or seals and/or screws for sealing and assembling the molded components to create the ventilator.

In one embodiment, the resultant molding is a single, two or three piece molding that is made of readily and commonly available materials such as plastic, silicon rubber, ABS (Acrylonitrile Butadiene Styrene), polysulphone or any other material that is either 'green'/disposable or reusable/sterilizable. Thus, the molding comprises a single casting from which a plurality of key ventilator components or elements are derived. The ventilator is disposable and therefore molded using material that is 'green' and disposable, e.g., by molding disposable ABS parts/components to form manifold/body and using silicone rubber for gaskets, diaphragms, valves and actuators of the ventilator system. In another embodiment the ventilator is reusable/sterilizable and therefore molded using material that can be effectively and repeatedly sterilized, e.g., by molding reusable polysulphone parts/components to form manifold/body and using silicone rubber for gaskets, diaphragms, valves and actuators to form a sterilizable ventilator system.

Figure 10:
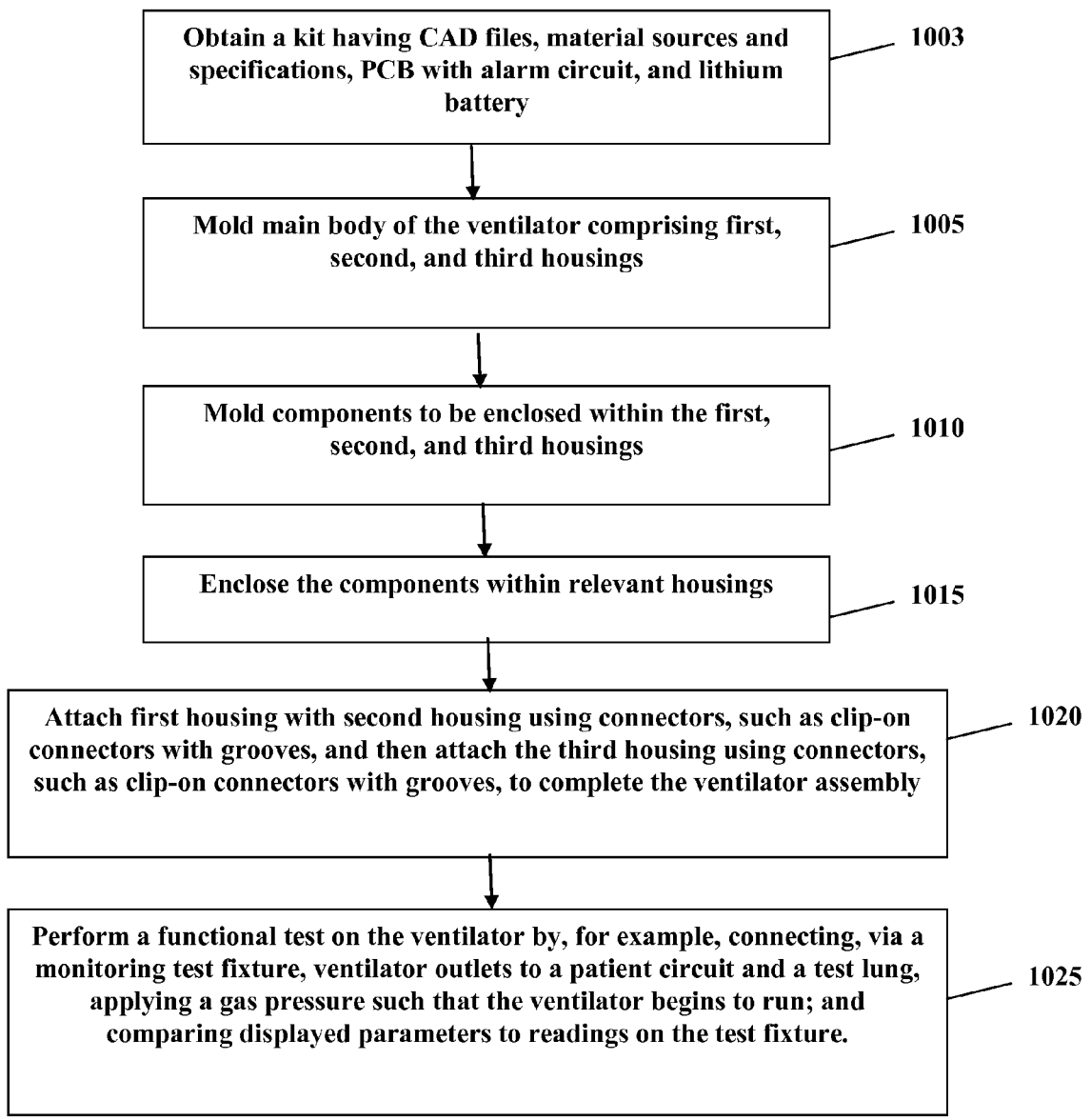
FIG. 10 is a flow chart showing exemplary steps of fabricating the ventilator according to one embodiment of the present invention.

FIG. 10 is a flow chart showing exemplary steps of fabricating the ventilator according to one embodiment of the present invention. Referring now to FIGS. 2 and 10 simultaneously, at step 1005 the main housing/body or manifold of the ventilator 200 of FIG. 2 is molded. In one embodiment, the main housing/body is molded in three pieces comprising a first housing 201, a second housing 202 and a third housing 203. At step 1010 the components to be enclosed in the housings 201, 202 and 203 are molded. In one embodiment, the components comprise of a first set comprising gas overpressure relief valve 202*a* and valve cover 202*b*, a second set comprising first diaphragm actuator 250 that further comprises actuator path or inhalation conduit 215 and branch conduit 245, a third set comprising "O"-ring 211, jet disc 206 and first jet cover 212 and a fourth set comprising bellows seal 207, first seal 208, top cover seal 213, electronics actuator 214, breathing rate control knob 225 and compressed gas interface 205. Persons of ordinary skill in the art should note that steps 1005 and 1010 are, in one embodiment, accomplished in single cast.

At step 1015 the plurality of component sets are enclosed within the relevant housings. In one embodiment, the first and second component sets are enclosed in the first housing 201; the third and fourth component sets are enclosed in the second housing 202 and the alarm printed circuit board (PCB) 240 is enclosed within the third housing 203. Thereafter, at step 1020 the housing 201 is attached to housing 202 which is then attached to housing 203 to form the ventilator assembly.

In one embodiment, clip-on connectors are employed to attach the ventilator components sets and relevant housings. In one embodiment, the clip-on connectors are formed as part of the moldings. In one embodiment, the clip-on connectors are integrated into the moldings such that two portions of the components or housing overlap to at least a minimum area and have features, such as but not limited to grooves, that engage within the overlapping edges.

According to an aspect of the present invention the quick and easy method of fabricating the ventilator is enabled by the ventilator being devoid of any proprietary parts or components and that the ventilator is sole-sourced thereby avoiding sourcing parts from multiple vendors. This also circumvents the impact of supply chain deficiencies on the fabrication of the ventilator, which may otherwise be detrimental, particularly in pandemic situations where most interstate and long range transportation is affected. The quick and easy method of fabricating the ventilator is also enabled by the fact that the final product is fabricated by obtaining a limited number of components and minimal electronics, as described above, most of which can be manufactured on the day when needed and require material and accessories that are simple and readily available anywhere is the world. Also, no machined parts/components are required.

In one embodiment, the quick and easy method of fabricating the ventilator is scalable and the number of units produced depends upon the size of the plant and the number of assemblers employed at the plant. In addition, the number of unit produced depends upon the rate at which the moldings are produced and the number of tools that produce the moldings. In one embodiment the ventilator of the present invention takes less than 15 minutes to assemble from the molded parts, requires no calibration, and can be tested in under 10 minutes.

In one embodiment, a test protocol is employed to ensure functionality of the ventilator of the present invention. In one embodiment, once the ventilator is assembled, a pressurized gas is applied to the ventilator. The molded portion of the ventilator is equipped, in one embodiment, with a standard threaded male connector formed within the molding which is employed to attached a conventional medical device oxygen hose. The hose, in turn, would connect to an oxygen supply ranging from 280 kPa to 450 kPa.

A leak test is also performed to ensure that the gas supply connections are free of leaks. The leak test is accomplished by pressurizing the system with the outlet occluded or blocked. The oxygen supply, which is equipped with a pressure gauge, is then turned on to raise the pressure and then turned off to isolate the input. The pressure is then monitored for approximately one minute, after which point in time, a drop in pressure less than a predetermined value would indicate success and thus, no leak.

In addition, a functional test to verify operability of the ventilator of the present invention is performed, as shown in FIG. 10. In the functional test, the outlets are connected to a patient circuit and a test lung of C20, R20 via a monitoring test fixture 1025. The ventilator will start to run when the gas supply is applied and the parameters displayed on the settings are subsequently compared to the readings on the test fixture. If within the specified, predetermined value ranges, then the ventilator is deemed operable.

According to an aspect of the present invention no calibration of the on-demand fabricated ventilator is required and a simple go/no go test is adequate to ensure a safe product which conforms to its specifications. The go/no go safety indicator is employed to indicate whether the unit passes the functional test and is safe to operate. In one embodiment, if all parameters that can be set on the control can be confirmed within specified ranges by the test fixture, then a test pass is confirmed. The unit is then packed for shipping with its accessories. In one embodiment, ranges for controls for the ventilator fabricated are set as follows:

Inspiratory pressure—10 $cmH_2O$ to 40 $cmH_2O$±2 $cmH_2O$ or 10%

PEEP—0 to 20 $cmH_2O$±2 $cmH_2O$ or 10%

Breathing rate—4 to 40 BPM±10%

Oxygen—50 to 100%±10%

According to an aspect of the present invention and referring to FIG. 10, a kit, package or factory-in-a-box (hereinafter referred to as the 'kit') is made available 1003 that in one embodiment comprises elements to enable on-demand development of necessary tooling for quick and easy manufacturing of the ventilator of the present invention anywhere/anytime in the world and in sufficiently large volumes to service at least 50% of the demand arising in a pandemic situation. In one embodiment, the kit is available 1003 in a build-a-factory concept comprising: CAD (Computer Aided Design) files for the tooling, that is the mold for casting the ventilator main housing/body and other components within the main housing/body, which includes clip-on connectors and fastening means; material sources and specifications for the ventilator; electronics schematics/PCBA along with a small lithium battery, such as, but not limited to those that are employed to power watches and calculators, to run breath detection and the alarm. In one embodiment, the material specification encompasses a broad range of readily available materials along with research into local sources for the materials depending on the region where the ventilator is to be fabricated. The material specifications are also dependent on whether the ventilator manufactured is disposable or reusable depending on situation. For example, the specifications and instructions are available for both ABS and polysulphone with different temperature and pressure directions.

In one embodiment, support elements such as drawings and manufacturing instruction, assembly instructions, test instructions, test equipment specifications, such as those described above, and user instructions are included in the kit in printed or audio/visual electronic format such as on read-only CD or a USB compatible flash memory card or drive. In another embodiment and more preferably, these support elements are accessible over the Internet and the kit only includes information of the website/server URL from where such support elements can be requisitioned.

In such embodiments where at least a portion of the unit is assembled post-shipment, local labor can be used to assemble devices. Thus, all hand tools and required instructions are made available according to the locality and in a plurality of local languages. Using local labor decreases import costs and would place actual deployment in the hands of the customer. Further, compliance to all local and government laws as well as required labeling can thus be performed on a local level reducing the burden of requirements from the FDA in the United States or other similar governing body.

In another embodiment, the kit or package of the present invention is available in buy-a-factory system where the actual tooling (e.g., the mold for casting the ventilator manifold/body and other components within the body/manifold) is included in the package along with the support elements to enable a quicker deployment of a mass manufacturing facility. In one embodiment, the buy-a-factory kit/package comprises: molds for hard plastic parts, such as but not limited to, and now referring to FIGS. 2 and 3, patient interface or connection port 220, gas over-pressure relief valve 202a and valve cover 202b, leak jet 265, actuator path or inhalation conduit 215, jet disc 206, bellows seal 207, compressed gas interface 205, branch conduit 245, first jet cover 212, electronics actuator 214, breathing rate control knob 225, exhaust port 235, gas control valve 310, inhalation conduit 315, flow control valve 325, exhaust port 335, and external PEEP valve 385; molds for soft plastic parts, such as but not limited to, and now referring to FIG. 2, gas over-pressure relief valve 202a and valve cover 202b, "O" ring 211, top cover seal 213, PCB 240, diaphragm actuator 250 for creating the molded soft silicon rubber parts that provide both a sealing function between the hard plastic parts and diaphragm actuators for timers and valve closure; an electronic PCBA with small lithium ion battery that is activated by the end user after assembly, as shown in FIG. 4; and assembly instructions which describe how ventilator components are fitted and pressed into place (without the need for special tools) in a stepwise fashion; how press fitting and fastening the final components together completes all seals; and how external labels are applied.

In one embodiment, pre-packaged kits that are shipped to distributors or customers are designed in such a way that the end product cannot be assembled incorrectly. For example, in one embodiment, design characteristics such as color coding and keyed interfaces are employed.

In addition, the critical functional components may be shipped as a tested assembly to the point of manufacture, which aids with regulatory compliance and device performance. Further, these critical assembly components may be serialized, tracked, and registered via a part and model number that is independent of the final assembly or product. Registering the critical assembly components beforehand may ensure acceptance of the final assembled product with non-critical components.

In such cases where the critical components are pre-assembled, an automated test device is included in the kits to ensure all design elements are in place and working according to design. In addition, diagnostics can be run by the critical components on the non-critical components to ensure compatibility and status of the non-critical assembly. Thus, in this checks and balance system, the critical assembly components will not function unless the non-critical assembly is working to specification and is compatible.

Further, the critical component can also specify a level of self-diagnosis that must be passed by the non-critical component before it will function. The diagnostic can also be run by the non-critical assembly, but the passing results would need to be authenticated by the critical assembly.

In another embodiment of the present invention, the whole assembled unit is shipped ready for immediate use in the field. The unit is fully tested and packaged. Thus, all processes are controlled by the manufacturer. However, all labor and labels are at the point of origin, and as such, there would be import restrictions and duties as required.

The above discussion is aimed towards providing several exemplary embodiments incorporating the novel aspects of the present invention and it should be understood that the foregoing illustration is not the only application where the present invention can be reduced down to practice. The present invention can be suitably modified to incorporate other possible embodiments as well. The scope of the invention is defined solely by the accompanying claims and within the scope of the claims; the present invention can be employed in various other situations.

We claim:

1. A kit for manufacturing a ventilator comprising:
   a first housing with internal structures formed to support enclosure of a first component set and a second component set, wherein the first housing further comprises at least one patient connection port and wherein the first housing comprises a first connector;
   a second housing with internal structures formed to support enclosure of a third component set and a fourth component set, wherein the second housing further comprises an exhaust port and wherein the second housing comprises a second connector that is configured to mate with the first connector; and
   a third housing with internal structures formed to support enclosure of an alarm printed circuit board (PCB), wherein the third housing comprises a third connector that is configured to mate with the second connector; and
   a printed circuit board (PCB) having an alarm circuit, wherein the first component set comprises a gas over-pressure relief valve and a valve cover, the second component set comprises a first diaphragm actuator and an inhalation conduit, the third component set comprises an O ring, Jet disc, and Jet cover, and the fourth component set comprises a bellows seal, first seal, top cover seal, electronics actuator, breathing rate control knob, and compressed gas interface, and wherein the ventilator without said alarm circuit being activated is adapted to operate without electricity.

2. The kit of claim 1, wherein the ventilator is disposable.

3. The kit of claim 1, wherein the first, second, third and fourth component sets are molded using silicone rubber.

4. The kit of claim 1 further comprising
   computer aided design (CAD) files defining a plurality of molds for casting the first, second, third and fourth component sets;
   material sources and specifications for the castings; and
   a lithium battery.

5. A method of manufacturing a ventilator comprising the steps of:
   obtaining a first housing with internal structures formed to support enclosure of a first component set and a second component set, wherein the first housing further comprises at least one patient connection port, wherein the first component set comprises a gas over-pressure relief valve and a valve cover, and wherein the second component set comprises first diaphragm actuator and inhalation conduit;
   obtaining a second housing with internal structures formed to support enclosure of a third component set and a fourth component set, wherein the second housing further comprises an exhaust port, wherein the third component set comprises an O ring, jet disc, and jet cover, and wherein the fourth component set comprises a bellows seal, first seal, top cover seal, electronics actuator, breathing rate control knob, and compressed gas interface;
   obtaining a third housing with internal structures formed to support enclosure of an alarm printed circuit board (PCB);
   obtaining the first, second, third and fourth component sets;
   obtaining a printed circuit board (PCB) having an alarm circuit; and
   enclosing the first and second component sets in the first housing; the third and fourth component sets in the second housing and the printed circuit board (PCB) within the third housing; and
   attaching the first housing, the second housing, and the third housing together, wherein the ventilator without said alarm circuit being activated is adapted to operate without electricity.

6. The method of manufacturing the ventilator of claim 5, wherein the ventilator is disposable.

7. The method of manufacturing the ventilator of claim 5, wherein ventilator is reusable.

8. The method of manufacturing the ventilator of claim 5, wherein the first, second, third and fourth component sets are molded using silicone rubber.

9. The method of manufacturing the ventilator of claim 5, wherein the first, second and third housings, the first, second, third and fourth component sets and the printed circuit board (PCB) are created using a kit comprising:
   computer aided design (CAD) files defining a plurality of molds for casting the first, second and third housings and the first, second, third and fourth component sets;
   material sources and specifications for the castings,
   the printed circuit board comprising the alarm circuit; and
   a lithium battery.

10. The method of manufacturing the ventilator of claim 5, wherein the first, second and third housings, the first, second, third and fourth component sets, and the printed circuit board (PCB) are created using a kit comprising:
    molds for casting the first, second and third housings and the first, second, third and fourth component sets;
    material sources and specifications for the castings,
    the printed circuit board having the alarm circuit, and
    a lithium battery.

11. The method of manufacturing the ventilator of claim 5, wherein clip-on connectors are integrated into moldings such that two portions of the components or housings overlap to at least a minimum area and have at least one feature that engages within overlapping edges.

12. The method of manufacturing the ventilator of claim 11, wherein the at least one feature includes grooves.

13. The method of manufacturing the ventilator of claim 5 further comprising the step of testing the ventilator.

14. The method of claim 13 wherein the testing step comprises:
    applying a pressurized gas to the ventilator;
    performing a leak test to ensure that gas supply connections are free of leaks; and
    performing a functional test to verify operability of the ventilator.

15. The method of claim 14, wherein said step of applying a pressurized gas to the ventilator comprises connecting a conventional medical device oxygen hose to both a standard threaded male connector formed within a molding and an oxygen supply ranging from 280 kPa to 450 kPa.

16. The method of claim 14, wherein said step of performing the leak test comprises pressurizing the ventilator with an outlet occluded or blocked, increasing an oxygen pressure, turning off an oxygen supply, and monitoring the pressure for approximately one minute.

17. The method of claim 14, wherein the functional test comprises connecting, via a monitoring test fixture, ventilator outlets to a patient circuit and a test lung; applying a gas pressure such that the ventilator begins to run; and comparing displayed parameters to readings on the test fixture.

* * * * *